US009088452B2

(12) United States Patent
Sicurello et al.

(10) Patent No.: US 9,088,452 B2
(45) Date of Patent: Jul. 21, 2015

(54) METHOD AND SYSTEM FOR PROVIDING DATA COMMUNICATION IN CONTINUOUS GLUCOSE MONITORING AND MANAGEMENT SYSTEM

(71) Applicant: Abbott Diabetes Care Inc., Alameda, CA (US)

(72) Inventors: Jeffery Mario Sicurello, Union City, CA (US); Hung Dinh, San Leandro, CA (US); Mark Kent Sloan, Redwood City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 148 days.

(21) Appl. No.: 13/756,158

(22) Filed: Jan. 31, 2013

(65) Prior Publication Data

US 2013/0211788 A1 Aug. 15, 2013

Related U.S. Application Data

(63) Continuation of application No. 12/770,715, filed on Apr. 29, 2010, now Pat. No. 8,368,556.

(60) Provisional application No. 61/173,599, filed on Apr. 29, 2009, provisional application No. 61/181,755, filed on May 28, 2009.

(51) Int. Cl.
*G08C 19/00* (2006.01)
*H04L 29/06* (2006.01)
(Continued)

(52) U.S. Cl.
CPC .......... *H04L 29/06176* (2013.01); *G06F 15/00* (2013.01); *H04L 65/00* (2013.01); *H04Q 9/00* (2013.01); *H04Q 2209/40* (2013.01); *H04Q 2209/823* (2013.01); *H04Q 2209/86* (2013.01)

(58) Field of Classification Search
CPC ... G06F 15/00; H04L 65/00; H04L 29/06176; H04Q 9/00
USPC ................................ 340/870.3; 600/347, 365
See application file for complete search history.

(56) References Cited

U.S. PATENT DOCUMENTS 3,581,062 A   5/1971 Aston
3,926,760 A   12/1975 Allen et al.
(Continued)

FOREIGN PATENT DOCUMENTS

CA   2605530   11/2006
DE   4401400   7/1995
(Continued)

OTHER PUBLICATIONS

Isermann, R., "Supervision, Fault-Detection and Fault-Diagnosis Methods—An Introduction", Control Engineering Practice, vol. 5, No. 5, 1997, pp. 639-652.
(Continued)

*Primary Examiner* — Peguy Jean Pierre
(74) *Attorney, Agent, or Firm* — Jackson & Co., LLP

(57) ABSTRACT

Method and apparatus for providing a data stream generator that generates a data stream associated with a monitored analyte level, and a radio frequency logic portion operatively coupled to the data stream generator, the radio frequency logic portion configured to generate a radio frequency data stream based on the data stream generated from the data stream generator, the radio frequency logic portion further including one or more finite state machines and a plurality of discrete digital logic circuits, the one or more finite state machines configured to control the plurality of digital logic circuits to generate the radio frequency data stream for wireless communication are provided. Systems and kits incorporating the same are also provided.

20 Claims, 21 Drawing Sheets

(51) Int. Cl.
*H04Q 9/00* (2006.01)
*G06F 15/00* (2006.01)

(56) References Cited

U.S. PATENT DOCUMENTS

| | | |
|---|---|---|
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,475,901 A | 10/1984 | Kraegen et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,324 A | 10/1987 | White |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,231,988 A | 8/1993 | Wernicke et al. |
| 5,245,314 A | 9/1993 | Kah et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,289,497 A | 2/1994 | Jacobson et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,794 A | 3/1995 | Gorman |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,462,051 A | 10/1995 | Oka et al. |
| 5,462,645 A | 10/1995 | Albery et al. |
| 5,497,772 A | 3/1996 | Schulman et al. |
| 5,499,243 A | 3/1996 | Hall |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,544,196 A | 8/1996 | Tiedemann, Jr. et al. |
| 5,568,806 A | 10/1996 | Cheney, II et al. |
| 5,569,186 A | 10/1996 | Lord et al. |
| 5,581,206 A | 12/1996 | Chevallier et al. |
| 5,582,184 A | 12/1996 | Erickson et al. |
| 5,586,553 A | 12/1996 | Halili et al. |
| 5,593,852 A | 1/1997 | Heller et al. |
| 5,600,301 A | 2/1997 | Robinson, III |
| 5,609,575 A | 3/1997 | Larson et al. |
| 5,628,310 A | 5/1997 | Rao et al. |
| 5,634,468 A | 6/1997 | Platt et al. |
| 5,653,239 A | 8/1997 | Pompei et al. |
| 5,659,454 A | 8/1997 | Vermesse |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,726,646 A | 3/1998 | Bane et al. |
| 5,733,259 A | 3/1998 | Valcke et al. |
| 5,748,103 A | 5/1998 | Flach et al. |
| 5,749,907 A | 5/1998 | Mann |
| 5,758,290 A | 5/1998 | Nealon et al. |
| 5,772,586 A | 6/1998 | Heinonen et al. |
| 5,791,344 A | 8/1998 | Schulman et al. |
| 5,804,047 A | 9/1998 | Karube et al. |
| 5,833,603 A | 11/1998 | Kovacs et al. |
| 5,891,049 A | 4/1999 | Cyrus et al. |
| 5,899,855 A | 5/1999 | Brown |
| 5,925,021 A | 7/1999 | Castellano et al. |
| 5,935,099 A | 8/1999 | Petterson |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,144,871 A | 11/2000 | Saito et al. |
| 6,162,611 A | 12/2000 | Heller et al. |
| 6,175,752 B1 | 1/2001 | Say et al. |
| 6,200,265 B1 | 3/2001 | Walsh et al. |

(56) References Cited

U.S. PATENT DOCUMENTS

| | | | |
|---|---|---|---|
| 6,212,416 | B1 | 4/2001 | Ward et al. |
| 6,219,574 | B1 | 4/2001 | Cormier et al. |
| 6,233,471 | B1 | 5/2001 | Berner et al. |
| 6,248,067 | B1 | 6/2001 | Causey, III et al. |
| 6,275,717 | B1 | 8/2001 | Gross et al. |
| 6,284,478 | B1 | 9/2001 | Heller et al. |
| 6,291,200 | B1 | 9/2001 | LeJeune et al. |
| 6,293,925 | B1 | 9/2001 | Safabash et al. |
| 6,294,997 | B1 | 9/2001 | Paratore et al. |
| 6,295,506 | B1 | 9/2001 | Heinonen et al. |
| 6,306,104 | B1 | 10/2001 | Cunningham et al. |
| 6,309,884 | B1 | 10/2001 | Cooper et al. |
| 6,329,161 | B1 | 12/2001 | Heller et al. |
| 6,359,270 | B1 | 3/2002 | Bridson |
| 6,360,888 | B1 | 3/2002 | McIvor et al. |
| 6,366,794 | B1 | 4/2002 | Moussy et al. |
| 6,377,828 | B1 | 4/2002 | Chaiken et al. |
| 6,379,301 | B1 | 4/2002 | Worthington et al. |
| 6,387,048 | B1 | 5/2002 | Schulman et al. |
| 6,400,974 | B1 | 6/2002 | Lesho |
| 6,405,066 | B1 | 6/2002 | Essenpreis et al. |
| 6,413,393 | B1 | 7/2002 | Van Antwerp et al. |
| 6,416,471 | B1 | 7/2002 | Kumar et al. |
| 6,418,346 | B1 | 7/2002 | Nelson et al. |
| 6,424,847 | B1 | 7/2002 | Mastrototaro et al. |
| 6,427,088 | B1 | 7/2002 | Bowman, IV et al. |
| 6,440,068 | B1 | 8/2002 | Brown et al. |
| 6,442,672 | B1 | 8/2002 | Ganapathy |
| 6,478,736 | B1 | 11/2002 | Mault |
| 6,484,046 | B1 | 11/2002 | Say et al. |
| 6,496,729 | B2 | 12/2002 | Thompson |
| 6,497,655 | B1 | 12/2002 | Linberg et al. |
| 6,514,718 | B2 | 2/2003 | Heller et al. |
| 6,520,326 | B2 | 2/2003 | McIvor et al. |
| 6,544,212 | B2 | 4/2003 | Galley et al. |
| 6,549,796 | B2 | 4/2003 | Sohrab |
| 6,551,494 | B1 | 4/2003 | Heller et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,975 | B1 | 5/2003 | Pool et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |
| 6,565,509 | B1 | 5/2003 | Say et al. |
| 6,571,128 | B2 | 5/2003 | Lebel et al. |
| 6,574,510 | B2 | 6/2003 | Von Arx et al. |
| 6,576,101 | B1 | 6/2003 | Heller et al. |
| 6,577,899 | B2 | 6/2003 | Lebel et al. |
| 6,579,231 | B1 | 6/2003 | Phipps |
| 6,579,690 | B1 | 6/2003 | Bonnecaze et al. |
| 6,585,644 | B2 | 7/2003 | Lebel et al. |
| 6,591,125 | B1 | 7/2003 | Buse et al. |
| 6,595,919 | B2 | 7/2003 | Berner et al. |
| 6,605,200 | B1 | 8/2003 | Mao et al. |
| 6,605,201 | B1 | 8/2003 | Mao et al. |
| 6,607,509 | B2 | 8/2003 | Bobroff et al. |
| 6,610,012 | B2 | 8/2003 | Mault |
| 6,611,206 | B2 | 8/2003 | Eshelman et al. |
| 6,627,154 | B1 | 9/2003 | Goodman et al. |
| 6,633,772 | B2 | 10/2003 | Ford et al. |
| 6,635,014 | B2 | 10/2003 | Starkweather et al. |
| 6,635,167 | B1 | 10/2003 | Batman et al. |
| 6,641,533 | B2 | 11/2003 | Causey, III et al. |
| 6,648,821 | B2 | 11/2003 | Lebel et al. |
| 6,654,625 | B1 | 11/2003 | Say et al. |
| 6,659,948 | B2 | 12/2003 | Lebel et al. |
| 6,668,196 | B1 | 12/2003 | Villegas et al. |
| 6,687,546 | B2 | 2/2004 | Lebel et al. |
| 6,689,056 | B1 | 2/2004 | Kilcoyne et al. |
| 6,694,191 | B2 | 2/2004 | Starkweather et al. |
| 6,695,860 | B1 | 2/2004 | Ward et al. |
| 6,698,269 | B2 | 3/2004 | Baber et al. |
| 6,702,857 | B2 | 3/2004 | Brauker et al. |
| 6,731,976 | B2 | 5/2004 | Penn et al. |
| 6,733,446 | B2 | 5/2004 | Lebel et al. |
| 6,735,183 | B2 | 5/2004 | O'Toole et al. |
| 6,735,479 | B2 | 5/2004 | Fabian et al. |
| 6,740,075 | B2 | 5/2004 | Lebel et al. |
| 6,741,877 | B1 | 5/2004 | Shults et al. |
| 6,746,582 | B2 | 6/2004 | Heller et al. |
| 6,758,810 | B2 | 7/2004 | Lebel et al. |
| 6,770,030 | B1 | 8/2004 | Schaupp et al. |
| 6,790,178 | B1 | 9/2004 | Mault et al. |
| 6,804,558 | B2 | 10/2004 | Haller et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,850,790 | B2 | 2/2005 | Berner et al. |
| 6,862,465 | B2 | 3/2005 | Shults et al. |
| 6,873,268 | B2 | 3/2005 | Lebel et al. |
| 6,878,112 | B2 | 4/2005 | Linberg et al. |
| 6,881,551 | B2 | 4/2005 | Heller et al. |
| 6,889,331 | B2 | 5/2005 | Soerensen et al. |
| 6,892,085 | B2 | 5/2005 | McIvor et al. |
| 6,895,263 | B2 | 5/2005 | Shin et al. |
| 6,895,265 | B2 | 5/2005 | Silver |
| 6,923,764 | B2 | 8/2005 | Aceti et al. |
| 6,931,327 | B2 | 8/2005 | Goode, Jr. et al. |
| 6,932,894 | B2 | 8/2005 | Mao et al. |
| 6,936,006 | B2 | 8/2005 | Sabra |
| 6,937,222 | B2 | 8/2005 | Numao |
| 6,940,403 | B2 | 9/2005 | Kail, IV |
| 6,941,163 | B2 | 9/2005 | Ford et al. |
| 6,950,708 | B2 | 9/2005 | Bowman IV et al. |
| 6,958,705 | B2 | 10/2005 | Lebel et al. |
| 6,968,294 | B2 | 11/2005 | Gutta et al. |
| 6,971,274 | B2 | 12/2005 | Olin |
| 6,974,437 | B2 | 12/2005 | Lebel et al. |
| 6,987,474 | B2 * | 1/2006 | Freeman et al. ............... 341/143 |
| 6,990,366 | B2 | 1/2006 | Say et al. |
| 6,997,907 | B2 | 2/2006 | Safabash et al. |
| 6,998,247 | B2 | 2/2006 | Monfre et al. |
| 7,003,336 | B2 | 2/2006 | Holker et al. |
| 7,003,340 | B2 | 2/2006 | Say et al. |
| 7,003,341 | B2 | 2/2006 | Say et al. |
| 7,009,511 | B2 | 3/2006 | Mazar et al. |
| 7,020,508 | B2 | 3/2006 | Stivoric et al. |
| 7,022,072 | B2 | 4/2006 | Fox et al. |
| 7,024,236 | B2 | 4/2006 | Ford et al. |
| 7,024,245 | B2 | 4/2006 | Lebel et al. |
| 7,029,444 | B2 | 4/2006 | Shin et al. |
| 7,041,068 | B2 | 5/2006 | Freeman et al. |
| 7,043,305 | B2 | 5/2006 | KenKnight et al. |
| 7,052,483 | B2 | 5/2006 | Wojcik |
| 7,056,302 | B2 | 6/2006 | Douglas |
| 7,058,453 | B2 | 6/2006 | Nelson et al. |
| 7,060,031 | B2 | 6/2006 | Webb et al. |
| 7,074,307 | B2 | 7/2006 | Simpson et al. |
| 7,081,195 | B2 | 7/2006 | Simpson et al. |
| 7,082,334 | B2 | 7/2006 | Boute et al. |
| 7,089,780 | B2 | 8/2006 | Sunshine et al. |
| 7,098,803 | B2 | 8/2006 | Mann et al. |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,118,667 | B2 | 10/2006 | Lee |
| 7,124,027 | B1 | 10/2006 | Ernst et al. |
| 7,125,382 | B2 | 10/2006 | Zhou et al. |
| 7,134,999 | B2 | 11/2006 | Brauker et al. |
| 7,136,689 | B2 | 11/2006 | Shults et al. |
| 7,154,398 | B2 | 12/2006 | Chen et al. |
| 7,155,290 | B2 | 12/2006 | Von Arx et al. |
| 7,171,274 | B2 | 1/2007 | Starkweather et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,203,549 | B2 | 4/2007 | Schommer et al. |
| 7,207,974 | B2 | 4/2007 | Safabash et al. |
| 7,225,535 | B2 | 6/2007 | Feldman et al. |
| 7,226,442 | B2 | 6/2007 | Sheppard et al. |

(56) References Cited

U.S. PATENT DOCUMENTS

| | | |
|---|---|---|
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,267,665 B2 | 9/2007 | Steil et al. |
| 7,276,029 B2 | 10/2007 | Goode, Jr. et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,408,132 B2 | 8/2008 | Wambsganss et al. |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,741,734 B2 | 6/2010 | Joannopoulos et al. |
| 7,771,352 B2 | 8/2010 | Shults et al. |
| 7,774,145 B2 | 8/2010 | Brauker et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,882,611 B2 | 2/2011 | Shah et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,948,369 B2 | 5/2011 | Fennell et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,978,063 B2 | 7/2011 | Baldus et al. |
| 7,999,674 B2 | 8/2011 | Kamen |
| 8,010,256 B2 | 8/2011 | Oowada |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 8,216,138 B1 | 7/2012 | McGarraugh et al. |
| 8,478,389 B1 * | 7/2013 | Brockway et al. ............ 600/509 |
| 8,509,107 B2 | 8/2013 | Sicurello et al. |
| 8,638,441 B2 * | 1/2014 | Egan et al. ................... 356/445 |
| 2001/0037366 A1 | 11/2001 | Webb et al. |
| 2001/0047127 A1 | 11/2001 | New et al. |
| 2002/0013522 A1 | 1/2002 | Lav et al. |
| 2002/0013538 A1 | 1/2002 | Teller |
| 2002/0019022 A1 | 2/2002 | Dunn et al. |
| 2002/0019584 A1 | 2/2002 | Schulze et al. |
| 2002/0042090 A1 | 4/2002 | Heller et al. |
| 2002/0049482 A1 | 4/2002 | Fabian et al. |
| 2002/0072784 A1 | 6/2002 | Sheppard et al. |
| 2002/0074162 A1 | 6/2002 | Su et al. |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0103499 A1 | 8/2002 | Perez et al. |
| 2002/0106709 A1 | 8/2002 | Potts et al. |
| 2002/0118528 A1 | 8/2002 | Su et al. |
| 2002/0128594 A1 | 9/2002 | Das et al. |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0076792 A1 | 4/2003 | Theimer |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0144579 A1 | 7/2003 | Buss |

(56) References Cited

U.S. PATENT DOCUMENTS

| | | |
|---|---|---|
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0204290 A1 | 10/2003 | Sadler et al. |
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216630 A1 | 11/2003 | Jersey-Willuhn et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0017300 A1 | 1/2004 | Kotzin et al. |
| 2004/0030531 A1 | 2/2004 | Miller et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0064068 A1 | 4/2004 | DeNuzzio et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0116786 A1 | 6/2004 | Iijima et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0254433 A1 | 12/2004 | Bandis et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0065464 A1 | 3/2005 | Talbot et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0287620 A1 | 12/2005 | Heller et al. |
| 2006/0001538 A1 | 1/2006 | Kraft et al. |
| 2006/0004270 A1 | 1/2006 | Bedard et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0129733 A1 | 6/2006 | Solbelman |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0202805 A1 | 9/2006 | Schulman et al. |
| 2006/0202859 A1 | 9/2006 | Mastrototaro et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0272652 A1 | 12/2006 | Stocker et al. |
| 2006/0287691 A1 | 12/2006 | Drew |
| 2006/0290496 A1 | 12/2006 | Peeters |
| 2006/0293607 A1 | 12/2006 | Alt et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0055799 A1 | 3/2007 | Koehler et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0106135 A1 | 5/2007 | Sloan et al. |
| 2007/0124002 A1 | 5/2007 | Estes et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |

(56) References Cited

U.S. PATENT DOCUMENTS

| | | |
|---|---|---|
| 2007/0249922 A1 | 10/2007 | Peyser et al. |
| 2007/0253021 A1 | 11/2007 | Mehta et al. |
| 2007/0255348 A1 | 11/2007 | Holtzclaw |
| 2007/0255531 A1 | 11/2007 | Drew |
| 2007/0258395 A1* | 11/2007 | Jollota et al. ............... 370/310 |
| 2007/0270672 A1 | 11/2007 | Hayter |
| 2007/0285238 A1 | 12/2007 | Batra |
| 2007/0299617 A1 | 12/2007 | Willis |
| 2008/0009304 A1 | 1/2008 | Fry |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045161 A1 | 2/2008 | Lee et al. |
| 2008/0045824 A1 | 2/2008 | Tapsak et al. |
| 2008/0055070 A1 | 3/2008 | Bange et al. |
| 2008/0058625 A1 | 3/2008 | McGarraugh et al. |
| 2008/0060955 A1 | 3/2008 | Goodnow |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0235469 A1 | 9/2008 | Drew |
| 2008/0244961 A1 | 10/2008 | Brister et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0278331 A1 | 11/2008 | Hayter et al. |
| 2008/0278332 A1 | 11/2008 | Fennell et al. |
| 2008/0278333 A1 | 11/2008 | Fennell et al. |
| 2008/0281171 A1 | 11/2008 | Fennell et al. |
| 2008/0281179 A1 | 11/2008 | Fennell et al. |
| 2008/0281840 A1 | 11/2008 | Fennell et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0085873 A1 | 4/2009 | Betts et al. |
| 2009/0099436 A1 | 4/2009 | Brister et al. |
| 2009/0105554 A1 | 4/2009 | Stahmann et al. |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0189738 A1 | 7/2009 | Hermle |

(56) References Cited

U.S. PATENT DOCUMENTS

| | | |
|---|---|---|
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0160759 A1 | 6/2010 | Celentano et al. |
| 2010/0168538 A1 | 7/2010 | Keenan et al. |
| 2010/0190435 A1 | 7/2010 | Cook et al. |
| 2010/0191085 A1 | 7/2010 | Budiman |
| 2010/0274515 A1 | 10/2010 | Hoss et al. |
| 2011/0004276 A1 | 1/2011 | Blair et al. |
| 2011/0031986 A1 | 2/2011 | Bhat et al. |
| 2011/0060530 A1 | 3/2011 | Fennell |
| 2011/0148905 A1 | 6/2011 | Simmons et al. |
| 2011/0152637 A1 | 6/2011 | Kateraas et al. |
| 2011/0257895 A1 | 10/2011 | Brauker et al. |
| 2011/0270112 A1* | 11/2011 | Manera et al. ............... 600/523 |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/047445 | 6/2004 |
| WO | WO-2004/061420 | 7/2004 |
| WO | WO-2005/041766 | 5/2005 |
| WO | WO-2005/089103 | 9/2005 |
| WO | WO-2006/024671 | 3/2006 |
| WO | WO-2006/064397 | 6/2006 |
| WO | WO-2008/138006 | 11/2008 |

OTHER PUBLICATIONS

Isermann, R., et al., "Trends in the Application of Model-Based Fault Detection and Diagnosis of Technical Processes", Control Engineering Practice, vol. 5, No. 5, 1997, pp. 709-719.

Kaplan, S. M., "Wiley Electrical and Electronics Engineering Dictionary", IEEE Press, 2004, pp. 141, 142, 548, 549.

Lortz, J., et al., "What is Bluetooth? We Explain the Newest Short-Range Connectivity Technology", Smart Computing Learning Series, Wireless Computing, vol. 8, Issue 5, 2002, pp. 72-74.

PCT Application No. PCT/US2010/033066, International Preliminary Report on Patentability and Written Opinion of the International Searching Authority mailed Nov. 10, 2011.

PCT Application No. PCT/US2010/033066, International Search Report and Written Opinion of the International Searching Authority mailed Jun. 29, 2010.

U.S. Appl. No. 12/770,715, Notice of Allowance mailed Dec. 12, 2012.

U.S. Appl. No. 12/770,715, Office Action mailed Jul. 17, 2012.

Israeli Patent Application No. 216037, Original Language and English summary of Official Action mailed Jul. 1, 2013.

* cited by examiner

| Byte | Contents |
|---|---|
| 0 | TxTime |
| 1 to 14 | Application payload |

FIGURE 11

| Received Packet Contents | | |
|---|---|---|
| 0 | Dotting pattern | Number of bits captured varies |
| 1 | Start indicator | 13 bits |
| 1 | Packed data | 15 symbols |
| 2 | Parity Symbols | 6 symbols |
| | Total | 21 symbols |

FIGURE 15

| Reed Solomon Block contents | | |
|---|---|---|
| 1 | Packed data | 15 bytes |
| 2 | TX ID, LSB | 1 byte |
| 3 | TX ID, least middle SB | 1 byte |
| 4 | TX ID, most middle SB | 1 byte |
| 5 | TX ID, MSB | 1 byte |
| | Zero pad | 230 bytes |
| | Parity Symbols | 6 bytes |
| | Total | 255 bytes |

FIGURE 12A

| Depadded Block contents | | |
|---|---|---|
| 1 | Packed data | 15 bytes |
| 2 | Parity Symbols | 6 bytes |
| | Total | 21 bytes |

FIGURE 12B

| Transmit Packet contents | | |
|---|---|---|
| 0 | 0x00<br>0x00<br>0x15<br>0x67 | 4 bytes |
| 1 | Depadded Block contents | 21 bytes |

FIGURE 12C

METHOD AND SYSTEM FOR PROVIDING DATA COMMUNICATION IN CONTINUOUS GLUCOSE MONITORING AND MANAGEMENT SYSTEM

RELATED APPLICATIONS

The present application is a continuation of U.S. patent application Ser. No. 12/770,715 filed Apr. 29, 2010, now U.S. Pat. No. 8,368,556, entitled "Method and System for Providing Data Communication in Continuous Glucose Monitoring and Management System", which claims priority under 35 U.S.C. §119(e) to U.S. provisional application No. 61/173,599 filed Apr. 29, 2009, entitled "Method and System for Providing Data Communication in Continuous Glucose Monitoring and Management System", and to U.S. provisional application No. 61/181,755 filed May 28, 2009, entitled "Device and Method for Creating Radio Frequency Data Stream with Minimal Logic", the disclosures of each of which are incorporated in their entirety by reference for all purposes.

BACKGROUND

The present disclosure relates to an in-vivo continuous glucose monitoring and management system. More specifically, the present disclosure relates to communication protocol for data communication between, for example, a transmitter and a receiver, in the continuous glucose monitoring and management systems for insulin therapy.

In data communication systems such as continuous glucose monitoring systems for insulin therapy, analyte levels such as glucose levels of a patient are continuously monitored, and the measured glucose levels are used to determine and adjust diabetes treatment. For example, real time values of measured glucose levels would allow for a more robust and accurate diabetes treatment. Indeed, accurately measured glucose levels of a diabetic patient would enable a more effective insulin therapy by way of a more timely bolus determination and administration.

Medical devices for use in such systems described above include semiconductor chips and other electronic components that are configured for wireless communication of the monitored analyte or glucose data. One implementation of such data communication in medical devices include application specific integrated circuits (ASICs) that provide a single chip implementation of radio frequency data stream generation for wireless communication. Typical ASICs however, include a high gate count, require a significant amount of power and generate unwanted digital noise that interferes with the operation and functioning of the radio frequency data stream.

In view of the foregoing, it would be desirable to provide medical devices that generate radio frequency data stream which has a lower gate count, lower power logic, and less induced digital noise than typical circuits and devices including the same.

SUMMARY

Embodiments include an apparatus comprising a data stream generator that generates a data stream associated with a monitored analyte level, and a radio frequency logic portion operatively coupled to the data stream generator, the radio frequency logic portion configured to generate a radio frequency data stream based on the data stream generated from the data stream generator, the radio frequency logic portion further including one or more finite state machines and a plurality of discrete digital logic circuits, the one or more finite state machines configured to control the plurality of digital logic circuits to generate the radio frequency data stream for wireless communication.

Embodiments include generating a data stream associated with a monitored analyte level with a data stream generator, and operatively coupling a radio frequency logic portion to the data stream generator, the radio frequency logic portion configured to generate a radio frequency data stream based on the data stream generated from the data stream generator, the radio frequency logic portion further including one or more finite state machines and a plurality of discrete digital logic circuits, the one or more finite state machines configured to control the plurality of digital logic circuits to generate the radio frequency data stream for wireless communication.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,167,818; and 7,299,082; U.S. Published Application Nos. 2004/0186365, now U.S. Pat. No. 7,811,231; 2005/0182306, now U.S Pat. No. 8,771,183; 2007/0056858, now U.S. Pat. No. 8,298,389; 2007/0068807, now U.S. Pat. No. 7,846, 311; 2007/0227911, now U.S. Pat. No. 7,887,682; 2007/0233013; 2008/0081977, now U.S. Pat. No. 7,618,369; 2008/0161666; and 2009/0054748, now U.S. Pat. No. 7,885,698; U.S. patent application Ser. Nos. 11/831,866, now U.S. Pat. No. 7,768,386; 11/831,881, now U.S. pat. No. 8,834,366; 11/831,895; 12/102,839; 12/102,844, now U.S. Pat. No. 8,140,142; 12/102,847; 12/102,855; 12/102,856; 12/152,636, now U.S. Pat. No. 8,260,558; 2/152,648, now U.S. Pat. No. 8,600,681; 12/152,650, now U.S. Pat. No. 8,444,560; 12/152,652, now U.S. Pat. No. 8,239,166; 12/152,657; 12/152,662; 12/152,670, now U.S. Pat. No. 7,996,158; 12/152,673; 12/363,712, now U.S. Pat. No. 8,346,335; 12/131,012; 12/242,823, now U.S. Pat. No. 8,219,173; 12/363,712, now U.S. Pat. No. 8,346,335; 12/393,921; 12/495,709; 12/698,124; 12/699,653; 12/699,844; 12/714,439; 12/761,372; and 12/761,387, now U.S. Pat. No. 8,497,777, and U.S. Provisional Application Ser. Nos. 61/230,686 and 61/227,967.

BRIEF DESCRIPTION OF THE DRAWINGS

FIG. 11 illustrates application data including the sensor data from the transmitter of the system shown in FIG. 1 in accordance with one embodiment of the present disclosure;

FIGS. 12A-12C illustrate a data packet table for Reed-Solomon encoding in the transmitter, a depadded data table, and a data packet transmitted from the transmitter, respectively, in accordance with one embodiment of the system of FIG. 1;

FIG. 15 illustrates a data packet at the receiver for demodulation in accordance with one embodiment of the present disclosure;

DETAILED DESCRIPTION

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Figure 1:
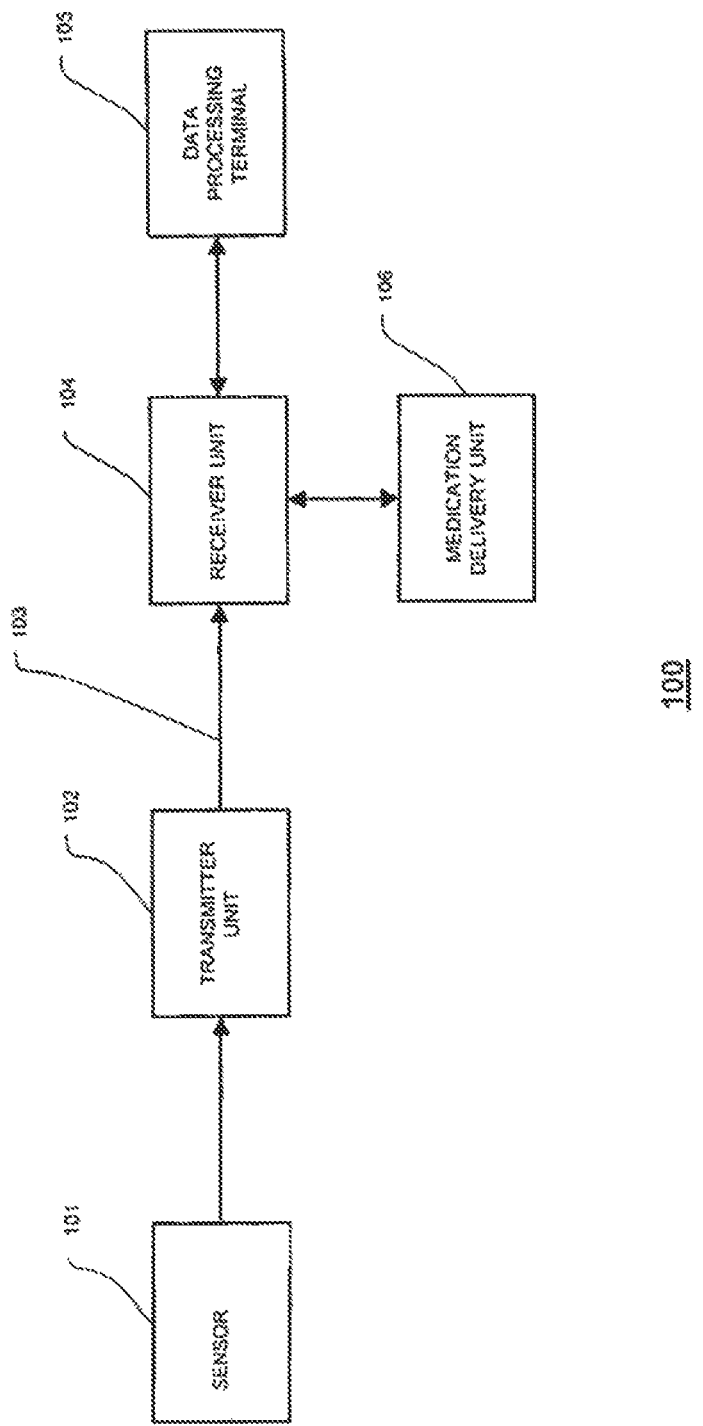
FIG. 1 is a block diagram of a continuous glucose monitoring and management system in accordance with embodiments of the present disclosure.

FIG. 1 is a block diagram of a continuous glucose monitoring and management system 100 in accordance with embodiments of the present disclosure. In such embodiment, the continuous glucose monitoring and management system 100 includes a sensor 101, a transmitter unit 102 coupled to the sensor 101, and a receiver unit 104 which is configured to communicate with the transmitter unit 102 via a communication link 103. The receiver unit 104 may be further configured to transmit data to a data processing terminal 105 for evaluating the data received by the receiver unit 104. Referring again to the Figure, also shown in FIG. 1 is a medication delivery unit 106 which is operatively coupled to the receiver unit 104. In one embodiment, the medication delivery unit 106 may be configured to administer a predetermined or calculated insulin dosage based on the information received from the receiver unit 104. For example, as discussed in further detail below, the medication delivery unit 106 in one embodiment may include an infusion pump configured to administer basal profiles to diabetic patients, as well as to determine and/or administer one or more suitable boluses for the diabetic patients.

Only one sensor 101, transmitter unit 102, communication link 103, receiver unit 104, and data processing terminal 105 are shown in the embodiment of the continuous glucose monitoring and management system 100 illustrated in FIG. 1. However, it will be appreciated by one of ordinary skill in the art that the continuous glucose monitoring and management system 100 may include one or more sensor 101, transmitter unit 102, communication link 103, receiver unit 104, and data processing terminal 105, where each receiver unit 104 is uniquely synchronized with a respective transmitter unit 102.

In one embodiment of the present disclosure, the sensor 101 is physically positioned on the body of a user whose glucose level is being monitored. The term user as used herein is intended to include humans, animals, as well as any other who might benefit from the use of the glucose monitoring and management system 100. The sensor 101 may be configured to continuously sample the glucose level of the user and convert the sampled glucose level into a corresponding data signal for transmission by the transmitter 102. In one embodiment, the transmitter unit 102 is mounted on the sensor 101 so that both devices are positioned on the user's body. The transmitter unit 102 performs data processing such as filtering and encoding on data signals, each of which corresponds to a sampled glucose level of the user, for transmission to the receiver unit 104 via the communication link 103.

In one embodiment, the continuous glucose monitoring and management system 100 is configured as a one-way RF communication path from the transmitter unit 102 to the receiver unit 104. In such embodiment, the transmitter unit 102 is configured to continuously and repeatedly transmit the sampled data signals received from the sensor 101 to the receiver unit 104, without acknowledgement from the receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the receiver unit 104 may be configured to detect such transmitted encoded sampled data signals at predetermined time intervals. While a uni-directional communication path from the transmitter unit 102 to the receiver unit 104 is described herein, within the scope of the present disclosure, a bi-directional communication between the transmitter unit 102 and the receiver unit 104 is also included. Indeed, the transmitter unit 102 may include a transceiver to enable both data transmission and reception to and from the receiver unit 104 and/or any other devices communicating over the communication link 103 in the continuous data monitoring and management system 100.

As discussed in further detail below, in one embodiment of the present disclosure the receiver unit 104 includes two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter demodulated with a local oscillator and filtered through a band-pass filter. The second section of the receiver unit 104 is a data processing section which is configured to process the data signals received from the transmitter unit 102 such as by performing data decoding, error detection and correction, data clock generation, and data bit recovery.

In operation, upon completing the power-on procedure, the receiver unit 104 is configured to detect the presence of the transmitter unit 102 within its range based on the strength of the detected data signals received from the transmitter unit 102. For example, in one embodiment, the receiver unit 104 is configured to detect signals with strength exceeding a predetermined level in order to identify the transmitter unit 102 from which the receiver unit 104 is to receive data. Alternatively, the receiver unit 104 in a further embodiment may be configured to respond to signal transmission for a predetermined transmitter identification information of a particular transmitter unit 102 such that, rather than detecting the signal strength of a transmitter unit 102 to identify the transmitter, the receiver unit 104 may be configured to detect a transmitted signal from a predetermined transmitter unit 102 based on the transmitted transmitter identification information corresponding to the pre-assigned transmitter identification information for the particular receiver unit 104.

In one embodiment, the identification information of the transmitter unit 102 includes a 16-bit ID number. In an alternate embodiment, the ID number may be a predetermined length including a 24-bit ID number or a 32-bit ID number. Further, any other length ID number may also be used. Thus, in the presence of multiple transmitter unit 102, the receiver unit 104 will only recognize the transmitter unit 102 which corresponds to the stored or reconstructed transmitter identification information. Data signals transmitted from the other transmitters within the range of the receiver unit 104 are considered invalid signals.

Referring again to FIG. 1, where the receiver unit 104 determines the corresponding transmitter unit 102 based on the signal strength of the transmitter unit 102, when the receiver unit 104 is initially powered-on, the receiver unit 104 is configured to continuously sample the signal strength of the data signals received from the transmitters within its range. If the signal strength of the data signals meets or exceeds the signal strength threshold level and the transmission duration threshold level, the receiver unit 104 returns a positive indication for the transmitter unit 102 transmitting the data signals. That is, in one embodiment, the receiver unit 104 is configured to positively identify the transmitter unit 102 after one data signal transmission. Thereafter, the receiver unit 104 is configured to detect positive indications for two consecutive data signal transmissions for a predetermined time period. At such point, after three consecutive transmissions, the transmitter unit 102 is fully synchronized with the receiver unit 104.

Upon identifying the appropriate transmitter unit 102, the receiver unit 104 begins a decoding procedure to decode the received data signals. In one embodiment, a sampling clock signal may be obtained from the preamble portion of the received data signals. The decoded data signals, which include fixed length data fields, are then sampled with the sampling clock signal. In one embodiment of the present disclosure, based on the received data signals and the time interval between each of the three data signal transmissions, the receiver unit 104 determines the wait time period for receiving the next transmission from the identified and synchronized transmitter unit 102. Upon successful synchronization, the receiver unit 104 begins receiving, from the transmitter unit 102, data signals corresponding to the user's detected glucose level. As described in further detail below, the receiver unit 104, in one embodiment, is configured to perform synchronized time hopping with the corresponding synchronized transmitter unit 102 via the communication link 103 to obtain the user's detected glucose level.

Referring yet again to FIG. 1, the data processing terminal 105 may include a personal computer, a portable computer such as a laptop or a handheld device (e.g., personal digital assistants (PDAs)), and the like, each of which is configured for data communication with the receiver via a wired or a wireless connection. Additionally, the data processing terminal 105 may further be connected to a data network (not shown) for storing, retrieving and updating data corresponding to the detected glucose level of the user.

Figure 2:
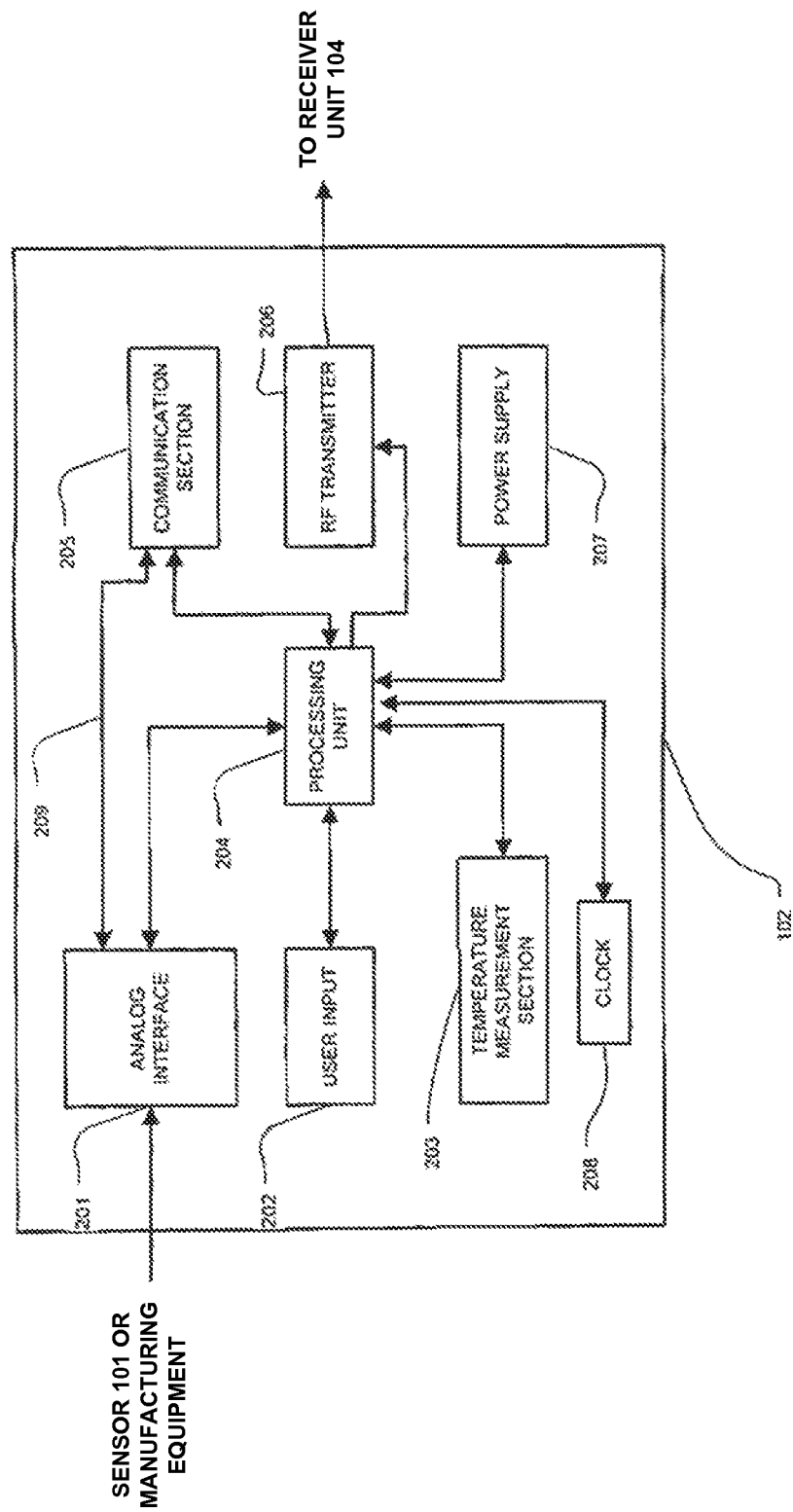
FIG. 2 is a block diagram of the transmitter unit of the system shown in FIG. 1 in accordance with embodiments of the present disclosure.

FIG. 2 is a block diagram of the transmitter unit 102 of the continuous glucose monitoring and management system 100 in accordance with embodiments of the present disclosure. The transmitter unit 102 includes an analog interface 201 configured to communicate with the sensor 101 (FIG. 1), a user input 202, and a temperature measurement section 203, each of which is operatively coupled to a transmitter processing unit 204 such as a central processing unit (CPU). Further shown in FIG. 2 are a transmitter serial communication section 205 and an RF transmitter 206, each of which is also operatively coupled to the transmitter processing unit 204. Moreover, a power supply 207 is also provided in the transmitter unit 102 to provide the necessary power for the transmitter unit 102. Additionally, as can be seen from the Figure, clock 208 is provided to, among others, supply real time information to the transmitter processing unit 204.

In one embodiment, a unidirectional input path is established from the sensor 101 (FIG. 1) and/or manufacturing and testing equipment to the analog interface 201, while a unidirectional output is established from the output of the RF transmitter 206. In this manner, a data path is shown in FIG. 2 between the aforementioned unidirectional input and output via a dedicated link 209 from the analog interface 201 to serial communication section 205, thereafter to the processing unit 204, and then to the RF transmitter 206. As such, in one embodiment, through the data path described above, the transmitter unit 102 is configured to transmit to the receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter 102 for operation upon completion of the manufacturing process as well as for direct communication for diagnostic and testing purposes.

Referring back to FIG. 2, the user input 202 includes a disable device that allows the operation of the transmitter unit 102 to be temporarily disabled, such as, by the user wearing the transmitter unit 102. In an alternate embodiment, the disable device of the user input 202 may be configured to initiate the power-up procedure of the transmitter unit 102.

As discussed above, the transmitter processing unit 204 is configured to transmit control signals to the various sections of the transmitter unit 102 during the operation of the transmitter unit 102. In one embodiment, the transmitter processing unit 204 also includes a memory (not shown) for storing data such as the identification information for the transmitter unit 102, as well as the data signals received from the sensor 101. The stored information may be retrieved and processed for transmission to the receiver unit 104 under the control of the transmitter processing unit 204. Furthermore, the power supply 207 may include a commercially available battery pack.

The physical configuration of the transmitter unit 102 is designed to be substantially water resistant, so that it may be immersed in non-saline water for a brief period of time without degradation in performance. Furthermore, in one embodiment, the transmitter unit 102 is designed so that it is substantially compact and light-weight, not weighing more than a predetermined weight such as, for example, approximately 18 grams. Furthermore, the dimensions of the transmitter unit 102 in one embodiment include 52 mm in length, 30 mm in width and 12 mm in thickness. Such small size and weight enable the user to easily carry the transmitter unit 102.

The transmitter unit 102 is also configured such that the power supply section 207 is capable of providing power to the transmitter for a minimum of three months of continuous operation after having been stored for 18 months in a low-power (non-operating) mode. In one embodiment, this may be achieved by the transmitter processing unit 204 operating in low power modes in the non-operating state, for example, drawing no more than approximately 1 µA. Indeed, in one embodiment, the final step during the manufacturing process of the transmitter unit 102 places the transmitter unit 102 in the lower power, non-operating state (i.e., post-manufacture sleep mode). In this manner, the shelf life of the transmitter unit 102 may be significantly improved.

Referring again to FIG. 2, the analog interface 201 of the transmitter unit 102 in one embodiment includes a sensor interface (not shown) configured to physically couple to the various sensor electrodes (such as, for example, working electrode, reference electrode, counter electrode, (not shown)) of the sensor 101 (FIG. 1) of the monitoring system 100. The analog interface section 201 further includes a potentiostat circuit (not shown) which is configured to generate the Poise voltage determined from the current signals received from the sensor electrodes. In particular, the Poise voltage is determined by setting the voltage difference between the working electrode and the reference electrode (i.e., the offset voltage between the working electrode and the reference electrode of the sensor 101). Further, the potentiostat circuit also includes a transimpedance amplifier for converting the current signal on the working electrode into a corresponding voltage signal proportional to the current. The signal from the potentiostat circuit is then low pass filtered with a predetermined cut-off frequency to provide anti-aliasing, and thereafter, passed through a gain stage to provide sufficient gain to allow accurate signal resolution detected from the sensor 101 for analog-to-digital conversion and encoding for transmission to the receiver unit 104.

Referring yet again to FIG. 2, the temperature measurement section 203 of the transmitter unit 102 is configured to monitor the temperature of the skin near the sensor insertion site. The temperature reading is used to adjust the glucose readings obtained from the analog interface 201. As discussed above, the input section 202 of the transmitter unit 102 includes the disable device which allows the user to temporarily disable the transmitter unit 102 such as for, example, to comply with the FAA regulations when aboard an aircraft. Moreover, in a further embodiment, the disable device may be further configured to interrupt the transmitter processing unit 204 of the transmitter unit 102 while in the low power, non-operating mode to initiate operation thereof.

The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver unit 104.

Figure 3:
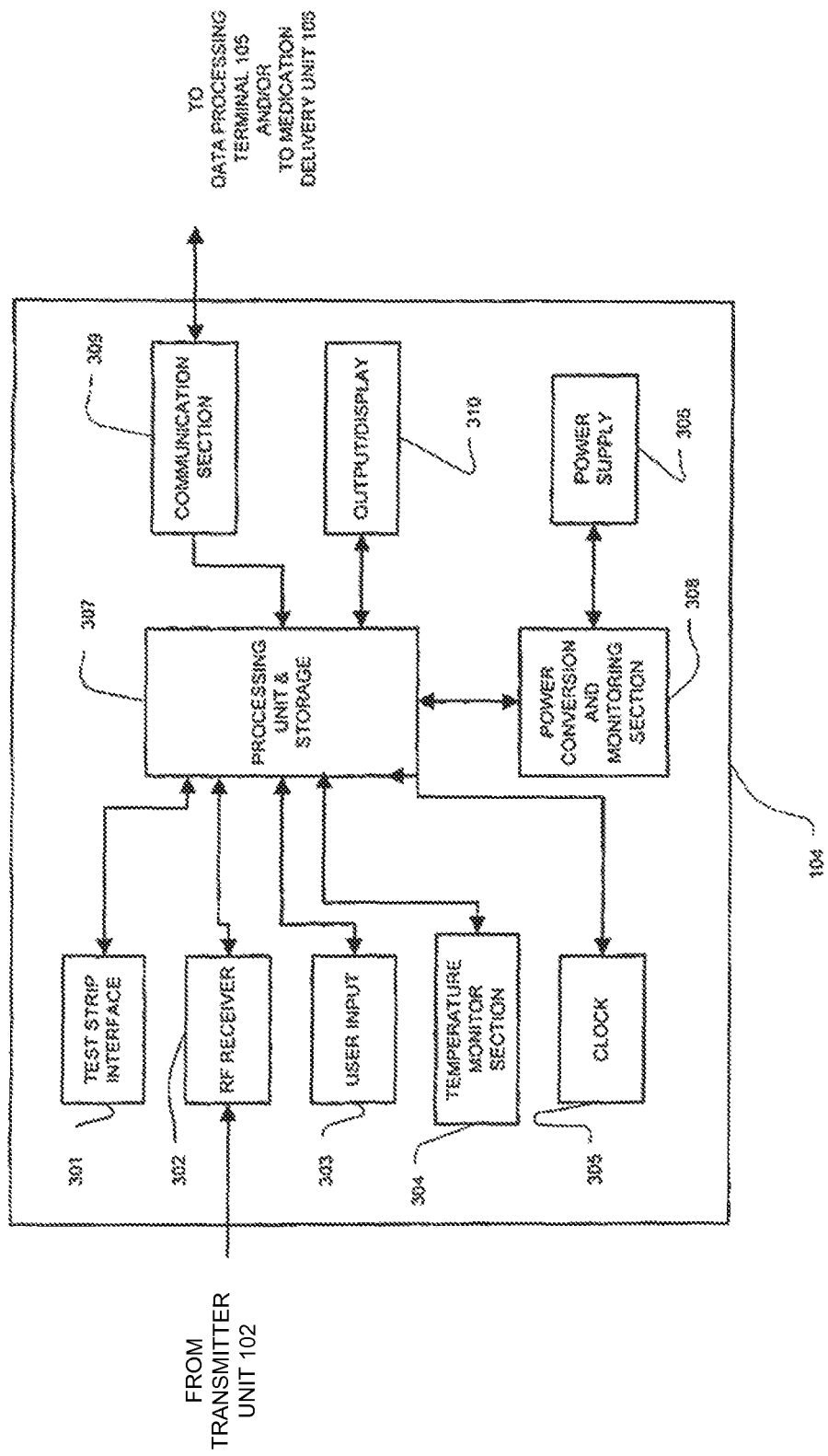
FIG. 3 is a block diagram of the receiver unit of the system shown in FIG. 1 in accordance with embodiments of the present disclosure.

FIG. 3 is a block diagram of the receiver unit 104 of the continuous glucose monitoring and management system 100 in accordance with one embodiments of the present disclosure. Referring to FIG. 3, the receiver unit 104 includes a blood glucose test strip interface 301, an RF receiver 302, an input 303, a temperature monitor section 304, and a clock 305, each of which is operatively coupled to a receiver processing unit 307. As can be further seen from the Figure, the receiver unit 104 also includes a power supply 306 operatively coupled to a power conversion and monitoring section 308. Further, the power conversion and monitoring section 308 is also coupled to the receiver processing unit 307. Moreover, also shown are a receiver communication section 309, and an output 310, each operatively coupled to the receiver processing unit 307.

In one embodiment, the test strip interface 301 includes a glucose level testing portion to receive a manual insertion of a glucose testing strip, and thereby determine and display the glucose level of the testing strip on the output 310 of the receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the receiver unit 104 is configured to allow the user to enter information into the receiver unit 104 as needed. In one aspect, the input 303 may include one or more keys of a keypad, a touch-sensitive screen, or a voice-activated input command unit. The temperature monitor section 304 is configured to provide temperature information of the receiver unit 104 to the receiver processing unit 307, while the clock 305 provides, among others, real time information to the receiver processing unit 307.

Each of the various components of the receiver unit 104 shown in FIG. 3 are powered by the power supply 306 which, in one embodiment, includes a battery. Furthermore, the power conversion and monitoring section 308 is configured to monitor the power usage by the various components in the receiver unit 104 for effective power management and to alert the user, for example, in the event of power usage which renders the receiver unit 104 in sub-optimal operating conditions. An example of such sub-optimal operating condition may include, for example, operating the vibration output mode (as discussed below) for a period of time thus substantially draining the power supply 306 while the processing unit 307 (thus, the receiver 104) is turned on. Moreover, the power conversion and monitoring section 308 may additionally be configured to include a reverse polarity protection circuit such as a field effect transistor (FET) configured as a battery activated switch.

The communication section 309 in the receiver unit 104 is configured to provide a bi-directional communication path from the testing and/or manufacturing equipment for, among others, initialization, testing, and configuration of the receiver unit 104. Serial communication section 309 can also be used to upload data to a computer, such as time-stamped blood glucose data. The communication link with an external device (not shown) can be made, for example, by cable, infrared (IR) or RF link. The output 310 of the receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the receiver unit 104 also includes an electro-luminescent lamp configured to provide backlighting to the output 310 for output visual display in dark ambient surroundings.

Referring back to FIG. 3, the receiver unit 104 in one embodiment, may also include a storage section such as a programmable, non-volatile memory device as part of the processing unit 307, or provided separately in the receiver unit 104, operatively coupled to the processing unit 307. The processing unit 307 is further configured to perform Manchester decoding as well as error detection and correction upon the encoded data signals received from the transmitter unit 102 via the communication link 103.

Figure 4A:
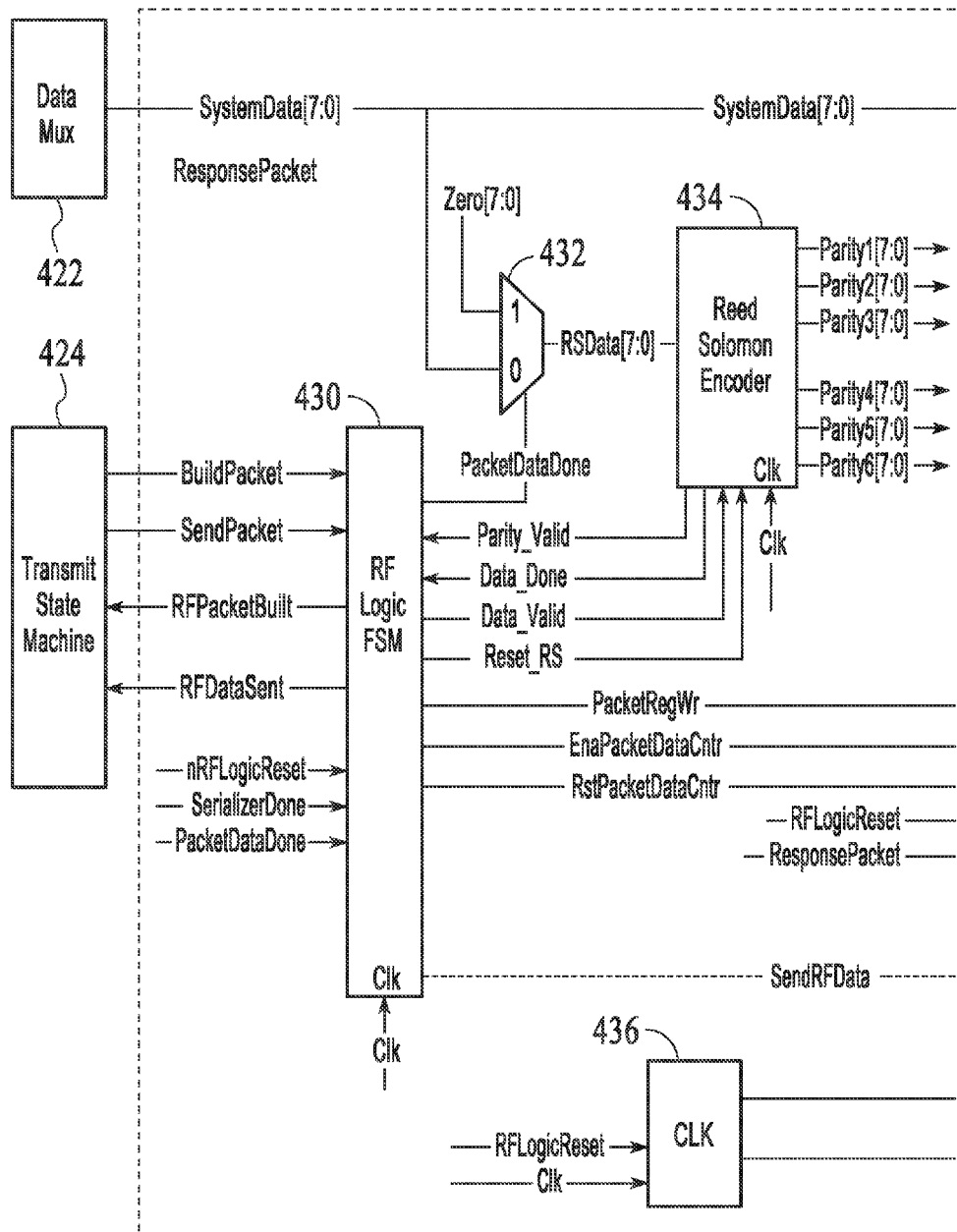
FIG. 4 is a diagram of a radio frequency data stream generator for use in the system of FIG. 1 in certain embodiments.
Figure 4B:
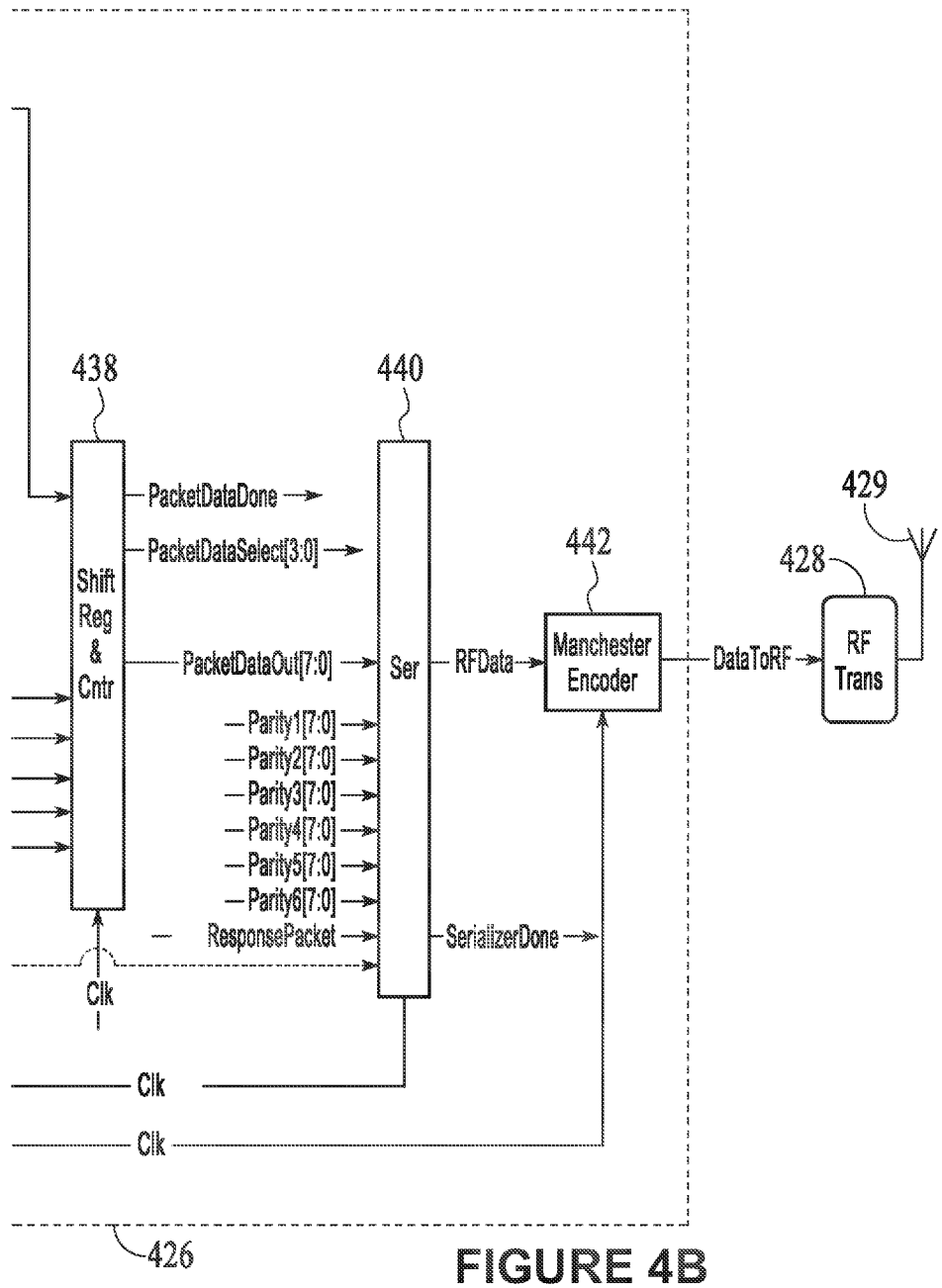

FIG. 4 is a diagram of a radio frequency data stream generator for use in the system of FIG. 1 in certain embodiments. Referring to FIG. 4, the radio frequency data stream generator 426, in certain embodiments, includes a radio frequency (RF) logic finite state machine (FSM) 430, a multiplexer 432, a Reed-Solomon encoder 434, a clock circuit 436, a set of RF data registers and a counter 438, a serializer 440, and a Manchester encoder 442. In some embodiments, the radio frequency data stream generator 426 (also known as RF logic section) is the data interface to the radio frequency (RF) transmitter 428. The radio frequency data stream generator 426 moves data packets from the data multiplexer 422, which, in certain embodiments, operates in a 32 KHz clock domain, to the RF data registers 438, which, in certain embodiments, operates in a 26 MHz clock domain. The radio frequency data stream generator 426 additionally adds the parity bits to the data packets using the Reed-Solomon encoder 434, adds the dotting pattern using the Manchester encoder 442, and presents the Manchester encoded bit stream to the RF transmitter 428.

Referring still to FIG. 4, the transmit state machine 424, which, in certain embodiments, operates in a 32 KHz clock domain, starts the radio frequency data stream generation sequence by turning on the clock circuit 436, which, in certain embodiments is a 26 MHz clock, and issuing a build packet command to the RF logic FSM 430. Data is stored in the set of RF data registers and counter 438 while the data packet is being built. The set of RF data registers and counter 438, in certain embodiments, contains eleven registers that hold the RF packet data, and each register is eight bits wide. The set of RF data registers and counter 438, in certain embodiments, also contains a counter to track the data stored by the RF logic FSM 430. Once the packet is built, the transmit state machine 424 issues a send packet command to the RF logic FSM 430, which instructs the RF logic FSM 430 to transmit the data packet to the RF transmitter 428. The sequence terminates when the RF logic FSM 430 issued an RF data sent signal back to the transmit state machine 424, indicating the data packet was transmitted via the RF transmitter 428.

In certain embodiments, the RF logic finite state machine 430 is in the 26 MHz clock domain. Unless the RF logic FSM 430 is processing data packets to generate the RF data stream, it is idle and is only called by the transmit state machine 424 (in the 32 KHz clock domain) when it is time to generate the RF data stream. The RF logic FSM 430 interfaces with the Reed-Solomon encoder 434, the data multiplexer 422 (also referred to as the packet engine), the RF data registers 438, the serializer 440, and the Manchester encoder 442, as shown in FIG. 4. The noise induced by the control logic side is reduced because all the packet data is stored in the RF logic and are operated on by logic in the same clock domain as the RF circuits so that most of the control logic is quiet as the tasks are handled by the RF logic.

Figure 5A:
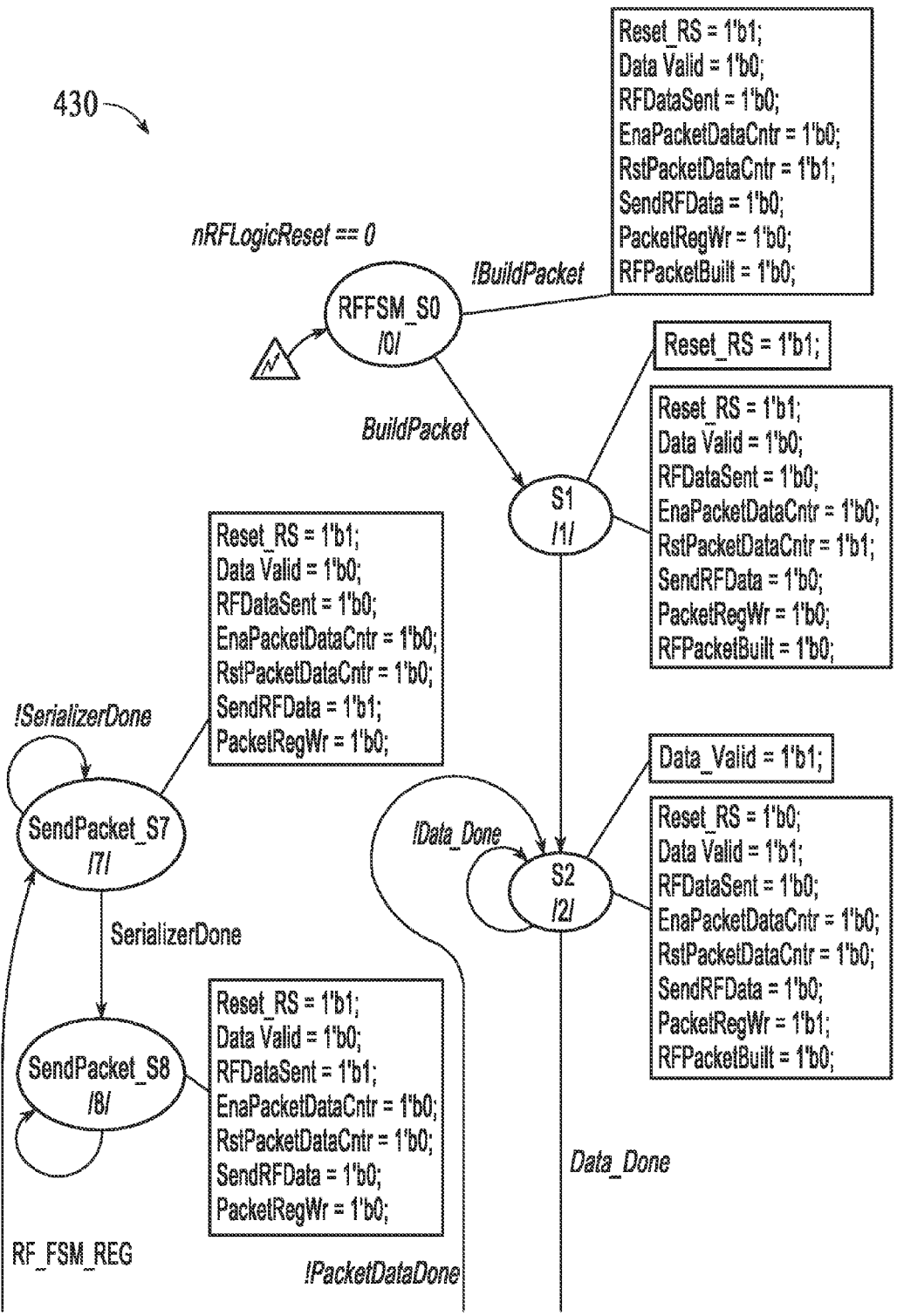
FIG. 5 is a state diagram illustrating the states of the radio frequency logic state machine of the radio frequency data stream generator of FIG. 4 in one embodiment.
Figure 5B:
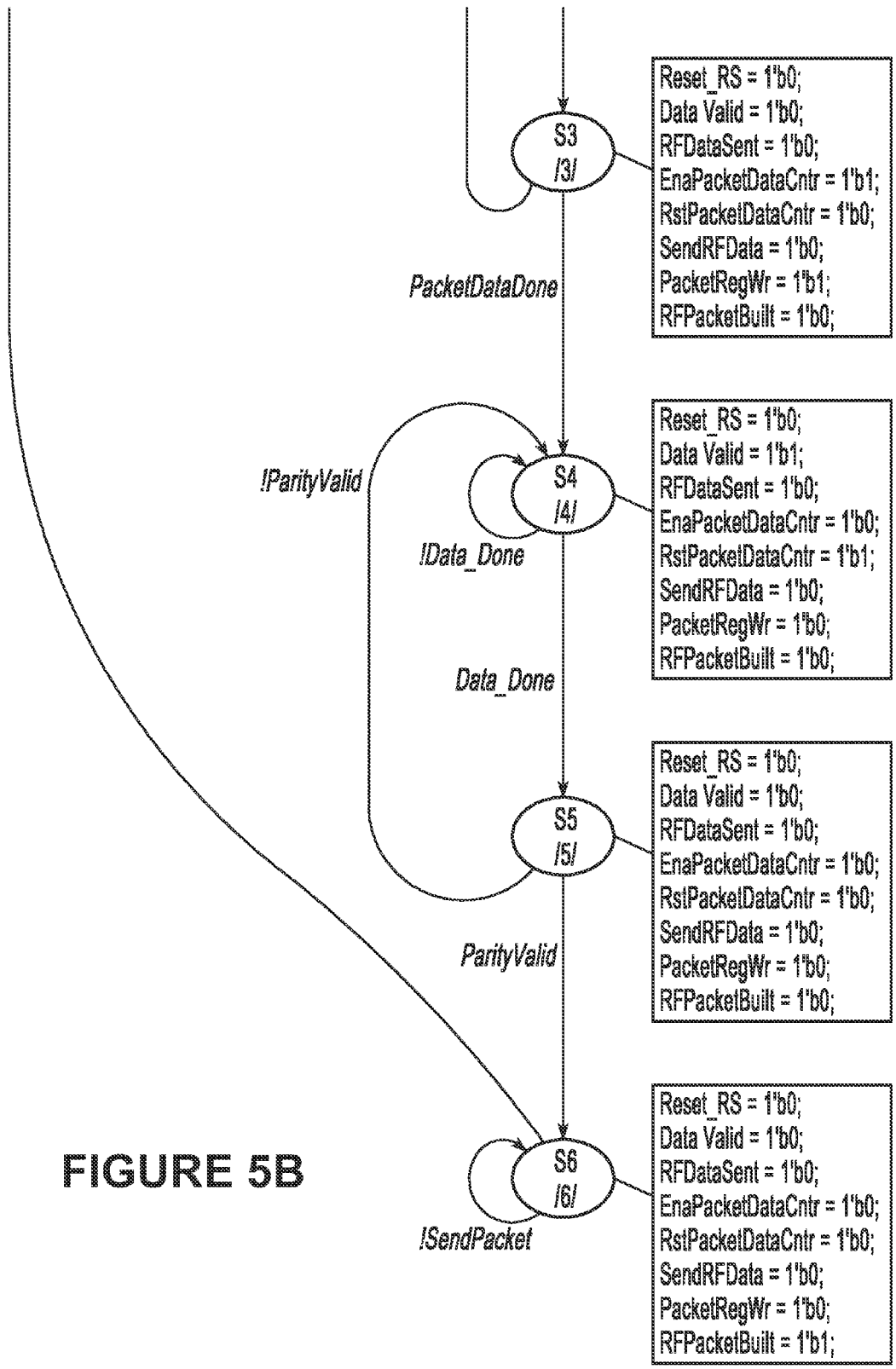

FIG. 5 is a state diagram illustrating the states of the radio frequency logic finite state machine of the radio frequency data stream generator of FIG. 4 in one embodiment. The state diagram of FIG. 5 of the radio frequency logic finite state machine 430 of FIG. 4 shows the states of the radio frequency logic finite state machine 430 (S0 to S8) and the signals at various states of the radio frequency logic finite state machine 430.

Figure 6:
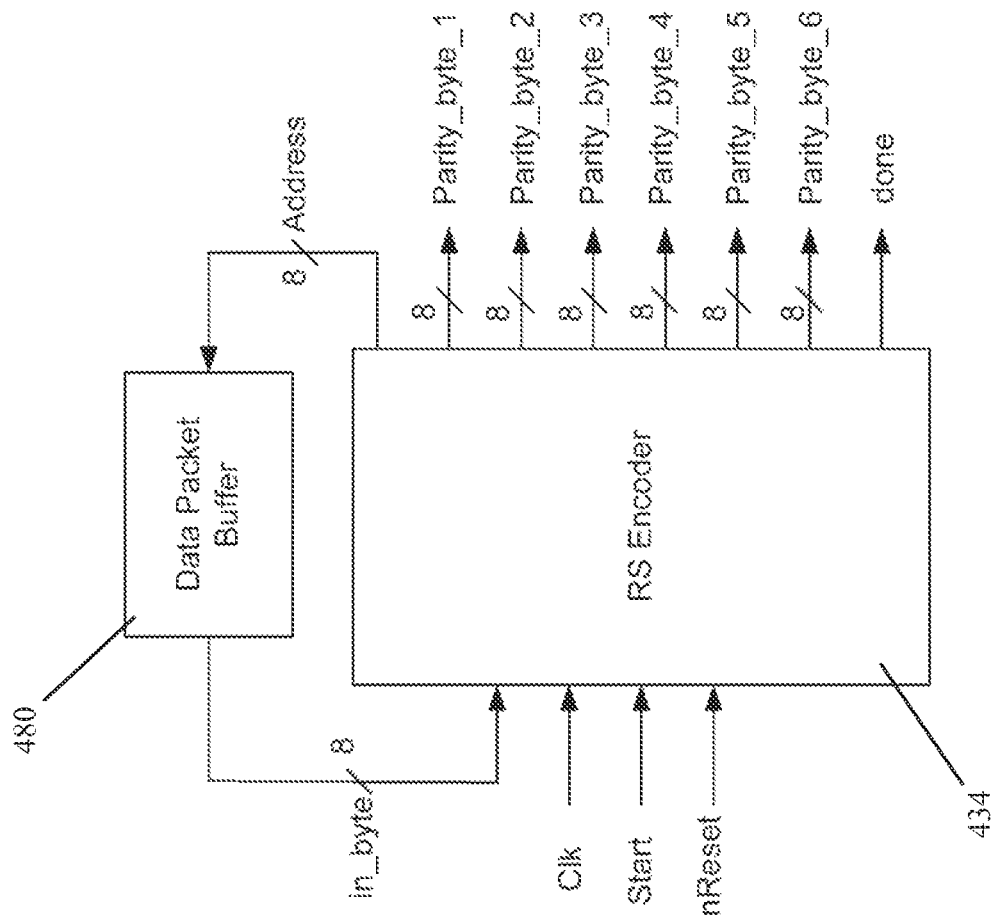
FIG. 6 illustrates an example Reed-Solomon encoder of the radio frequency data stream generator of FIG. 4 in one embodiment.

FIG. 6 illustrates an example Reed-Solomon encoder of the radio frequency data stream generator of FIG. 4 in one embodiment. In one embodiment, the Reed-Solomon encoder 434 may be connected to a data packet buffer 480, as shown in FIG. 6. In this embodiment, the Reed-Solomon encoder 434 receives a 249 byte message and produces six parity bytes (Parity_byte_1 to Parity_byte_6). The input signals to the Reed-Solomon encoder include an nReset signal, which is an active low signal that resets the Reed-Solomon encoder, a CLK or clock signal, which, in one embodiment, is a 13 MHz system clock signal, a Start signal, which provides a one clock period active high signal from, for example, the RF logic FSM 430 (FIG. 4) to inform the Reed-Solomon encoder 434 to start the encoding process by resetting all the polynomial and state registers to zero. Further, the Reed-Solomon encoder 434 receives an in_byte eight-bit message that is to be encoded.

Referring still to FIG. 6, the Reed-Solomon encoder 434 includes output signals Parity_byte_1 to Parity_byte_6, which are the six parity bytes that are generated as a result of the encoding of the 249 byte message, a done output bit to communicate to the RF logic FSM 430 (FIG. 4) that the encoding process is completed, and an eight-bit Address signal that can be sent to the data packet buffer 480 to retrieve the 19 bytes of the 249 byte message, while the rest of the 230 bytes of the 249 byte message are zero and generated by the Reed-Solomon encoder 434.

Figure 7:
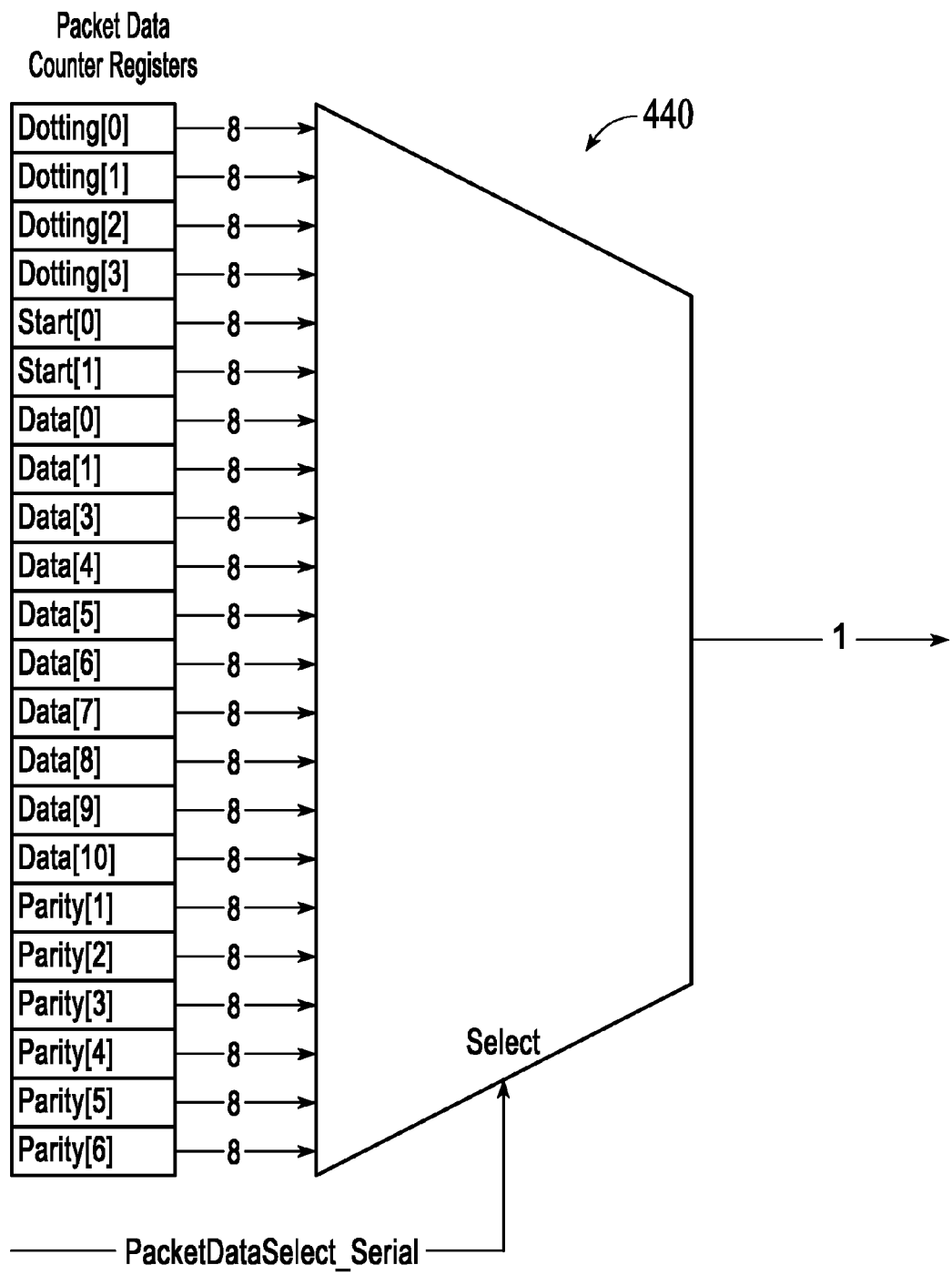
FIG. 7 illustrates an example serializer of the radio frequency data stream generator of FIG. 4 in one embodiment.

FIG. 7 illustrates an example serializer of the radio frequency data stream generator of FIG. 4. Referring to FIG. 7, the serializer 440 is, in effect, a large parallel to serial converter in which data is presented at the input of a large multiplexer. The data is then multiplexed out one bit-at-a-time, for example, at a baud rate of 19.2 Kbit/sec. In certain embodiments, the size of the data packet is eleven data bytes for a normal packet and six data bytes for a response packet. The serializer 440 counter termination count varies depending on the type of packet. For a normal packet, the count is 183 (for 184 bits) and for a response packet, the count is 143 (for 144 bits).

Figure 8:
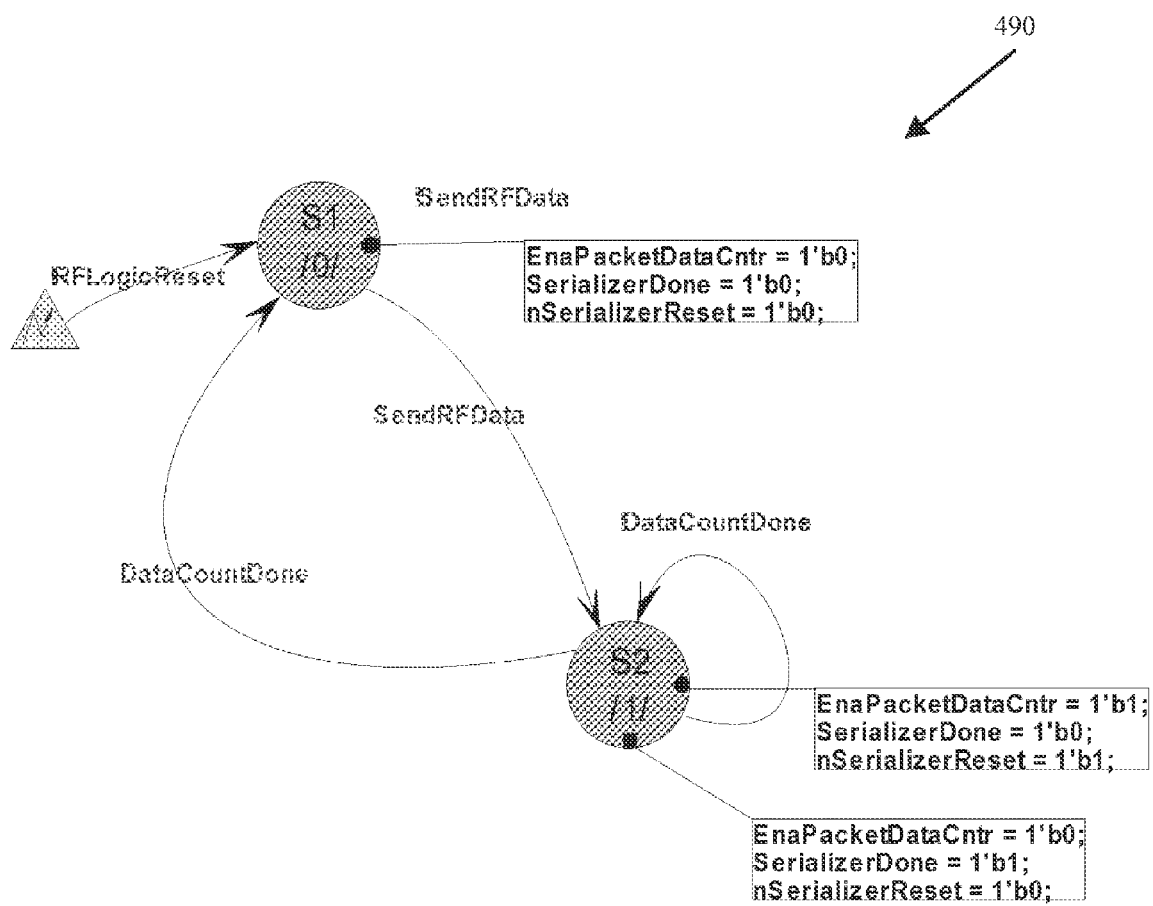
FIG. 8 is a state diagram illustrating the states of the serializer of the radio frequency data stream generator of FIG. 4 in one embodiment.

FIG. 8 is a state diagram illustrating the states of the serializer of the radio frequency data stream generator of FIG. 4 in one embodiment. The state diagram of FIG. 8 is an example implementation of a serializer state machine 490 that is part of the radio frequency data stream generator of FIG. 4 in which the two states of the serializer and the signals during each state or state transition are shown.

Figure 9:
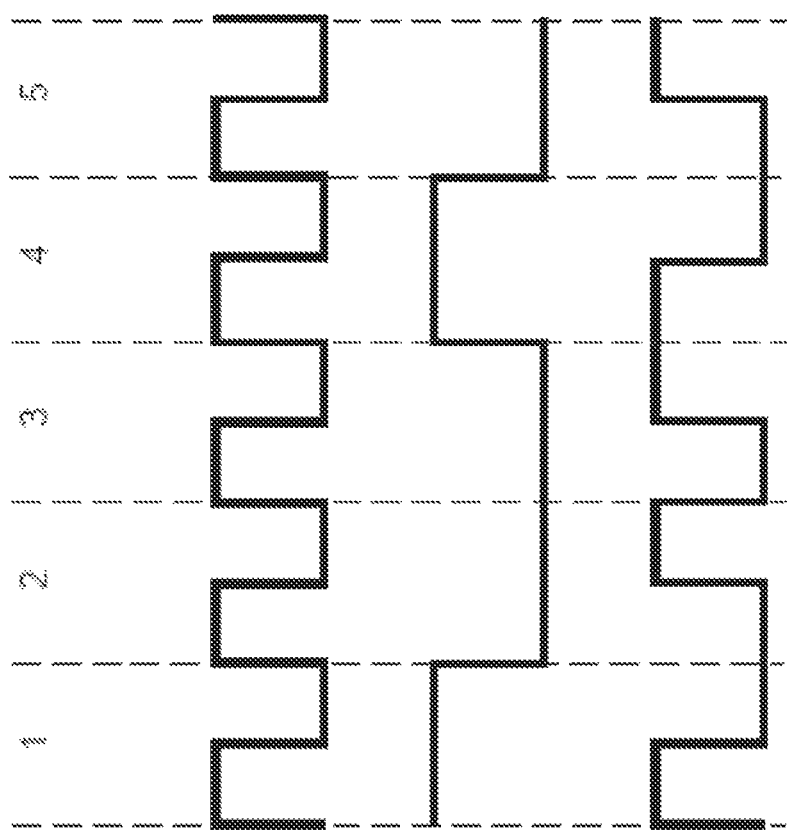
FIG. 9 illustrates an example implementation of the Manchester encoder of the radio frequency data stream generator of FIG. 4 in one embodiment.

FIG. 9 illustrates an example implementation of the Manchester encoder of the radio frequency data stream generator of FIG. 4 in one embodiment. Referring to FIG. 9, data from the serializer 440 (FIG. 4) is Manchester encoded by the Manchester encoder 442 (FIG. 4). The data is encoded such that NRZ 0=01 and NRZ 1=10, as illustrated in FIG. 9. This way each bit of data produces a Manchester symbol of two bits where the Manchester clock is, for example, 38.4 KHz or twice the bit clock rate. In one embodiment, both the serializer 440 and Manchester encoder 442 clocks are divided versions of the 26 MHz clock of the RF data stream generator.

Figure 10:
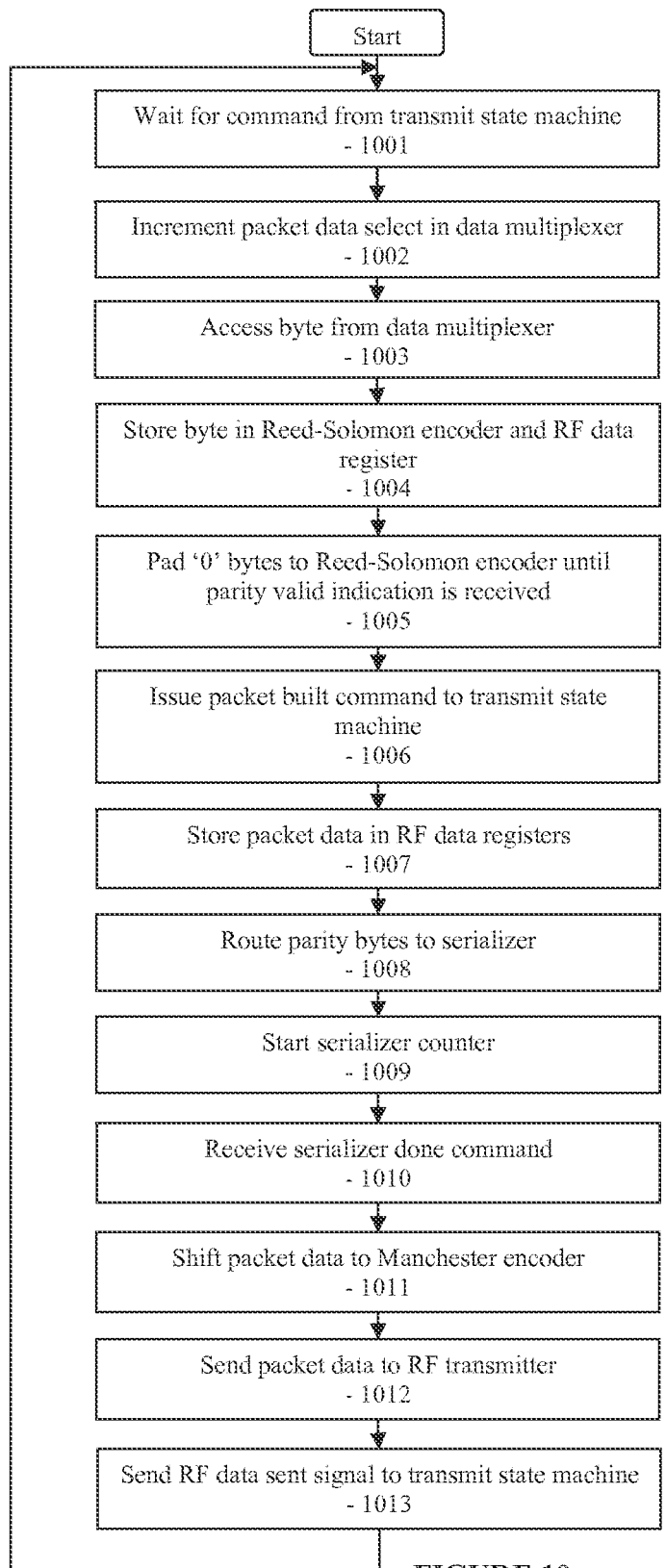
FIG. 10 is a flowchart illustrating a method for generating a radio frequency data stream in one embodiment.

FIG. 10 is a flowchart illustrating a method for generating a radio frequency data stream in one embodiment. RF data streams generated may include glucose monitoring system data, such as current and/or historical sensor signal data. Referring to FIGS. 10 and 4, the RF logic FSM 430 waits in state 0, or an idle state, until it receives a build packet command from the transmit state machine 424 (1001). The data multiplexer 422 contains all the RF packet data values, and the data values are arranged such that when the select line, i.e. PacketDataSelect[3:0] is incremented, the data appears on SystemData[7:0] in the proper format and sequence. The transmit state machine 424 and the RF logic FSM 430 do not control the packet formatting. As the packet data, i.e. PacketDataSelect[3:0], is incremented by the RF logic FMS 430 (1002), the RF logic FSM 430 accesses a byte from the data multiplexer 422 (1003). This byte is then stored in the Reed-Solomon encoder 434 for parity generation and also stored in the corresponding RF data register 438 (1004).

Once all the data is sent, the RF logic FSM pads '0' bytes to the Reed-Solomon encoder 434 until the Reed-Solomon encoder 434 issues a parity valid indication (1005). Once the packet is built, the RF logic FSM 430 advances to state 6 and issues a packet build command to the transmit state machine 424 (1006). At this point, all the packet data is stored in the RF data registers 438 (1007), the parity bytes are routed to the serializer 440 (1008), and the packet header is hardwired internal to the serializer 440. The serializer 440 is a large N to 1 multiplexer that sends out the data serially as the select line is incremented.

Still referring to FIGS. 10 and 4, when the transmit state machine 424 issues a send packet command, the RF logic FSM 430 advances to state 7 and starts the serializer counter (1009). When the serializer 440 reaches a max count, a serializer done command is sent to the RF logic FSM 430 (1010). The data is shifted out to the Manchester encoder 442 (1011), for example at a baud rate of 19.2 k. The packet data is then sent to the RF transmitter 428 (1012). The RF logic FSM 430 then advances to state 8 and issues an RF data sent signal to the transmit state machine 424 (1013). The RF logic FSM 430 then goes back to state 0 to wait for the next command for data packet generation process from the transmit state machine 424.

FIG. 11 illustrates an application data packet including the sensor data from the transmitter of the system shown in FIG. 1 in accordance with one embodiment of the present disclosure. Referring to FIG. 11, in one embodiment, each data packet from the transmitter unit 102 includes 15 bytes as shown in the Figure. For example, the first byte (zero byte) corresponds to the transmitter unit 102 transmit time information ("TxTime") which is a protocol value and is configured to start at zero and incremented with every data packet. In one embodiment, the transmit time (TxTime) data is used for synchronizing the transmit window hopping and error correction as discussed in further detail below. Referring back to FIG. 11, the transmit data packet also includes bytes 1 to 14 which comprise the application payload that includes signal representation of the glucose values measured by the sensor 101, and which is to be encoded with transmission protocol information and transmitted to the receiver unit 104. For example, in one embodiment, the transmission data packet is Reed-Solomon encoded and transmitted to the receiver unit 104, which is configured to detect and correct up to 3 symbol errors. It should be noted that the Reed-Solomon encoding discussed herein may be configured to perform forward error correction encoding on the transmission data packet prior to transmission to the receiver unit 104.

FIGS. 12A-12C illustrate a data packet table for Reed-Solomon encoding in the transmitter, a depadded data table, and a data packet transmitted from the transmitter, respectively, of the continuous glucose monitoring and management system of FIG. 1 in accordance with one embodiment. Referring to FIG. 12A, it can be seen that the Reed-Solomon encoded data block contents include 15 bytes of packed data (FIG. 11), one byte of the least significant bit (LSB) of the transmitter identification information (TxID), one byte of the least middle significant bit of the transmitter identification information (TxID), one byte of the most middle significant bit of the transmitter identification information (TxID), one byte of the most significant bit (MSB) of the transmitter identification information (TxID), 230 bytes of zero pads, 6 bytes of parity symbols, to comprise a total of 255 bytes.

In one embodiment, the Reed-Solomon encode procedure at the transmitter unit 102 uses 8 bit symbols for a 255 symbol block to generate the 6 parity symbols. The encoding procedure may include the encoding of the transmitter identification information into the parity symbols. The transmitter unit 102 (FIG. 1) in one embodiment is configured to build the data portion (15 bytes of packed data) of the data block shown in FIG. 12A (for example, using a virtual realization of the table). The transmitter unit 102 is configured to remove the 230 bytes of zero pads, and the 4 bytes of transmitter identification information (TxID), resulting in the 21 bytes of depadded data block including the 15 bytes of packed data and the 6 bytes of parity symbols as shown in FIG. 12B.

In one embodiment, the transmitter identification information (TxID) is not included in the transmitted data transmitted from the transmitter unit 102 (FIG. 1) to the receiver unit 104. Rather, the receiver unit 104 may be configured to determine the transmitter identification information (TxID) from the received data by using Reed-Solomon decoding. More specifically, when decoding the first data packet received from a transmitter unit 102, the receiver unit 104 may be configured to set the value corresponding to the transmitter identification information (TxID) to zero, and to indicate to the Reed-Solomon decoder that the transmitter identification information (TxID) is known to be incorrect. The Reed-Solomon decoder may then be configured to use this information to more effectively "correct" during the error correction procedure, and therefore to recover the transmitter identification information (TxID) from the received data. Indeed, in subsequent data packets, the received pads and the received data packet with the known transmitter identification information (TxID) are used to facilitate with the error detection.

Referring back to FIG. 12C, a link prefix is added to the depadded data block to complete the data packet for transmission to the receiver unit 104 (FIG. 1). The link prefix allows the receiver unit 104 to align the byte boundaries associated with the transmitted data from the transmitter unit 102 for Reed-Solomon decoding as described in further detail below. More specifically, as shown in FIG. 12C, the transmitter unit 102 is configured to add 4 bytes of link prefix (0x00, 0x00, 0x15, and 0x67) to the 21 bytes of depadded data block to result in 25 bytes of data packet. In this manner, once powered up and enabled in operational mode, the transmitter unit 102 is configured to transmit the 25 byte data packet once every minute. More specifically, in one embodiment, the transmitter unit 102 may be configured to Manchester encode the data at 2 Manchester bits per data bit (0=10; 1=01), and transmit the Manchester bits at 20,000 Manchester bits per second. It should be noted here that the Manchester encoding in one embodiment is configured to encode the data clock with the transmitted data. Further, it may be configured to shift the frequency content up so that there is no DC (direct current) content. The transmitter unit 102 may be configured to transmit the data packets with the most significant bit—byte zero first.

In this manner, in one embodiment of the present disclosure, the transmitter unit 102 may be configured to transmit a data packet once per minute, where the time between each data packet transmission may range between 50 to 70 seconds. In one embodiment, the transmitter may be configured to maintain a minute tick reference to schedule transmit windows as discussed in further detail below. The first data packet then may be scheduled relative to that time.

More specifically, the time that the data packet is transmitted by the transmitter unit 102 may vary from minute to minute. For example, in one embodiment, the first 10 seconds after a minute tick are divided into time windows each being 25 milliseconds wide, and numbered from 0 to 399. The transmitter unit 102 may then be configured to select the transmit window based upon a predetermined transmit configuration.

In one embodiment, the transmitter unit 102 may be configured to select a transmit window based on the transmitter identification information (TxID) and the transmit time information (TxTime). As discussed in further detail below, the transmit time (TxTime) represents a value that starts at zero and increments to 256 for each data packet sent. When the transmit time (TxTime) is equal to zero, a pseudo random number generator is seeded with the transmitter identification information (TxID). Then, for each minute, the pseudo random number generator may be used to generate the transmit window for that minute.

Figure 13:
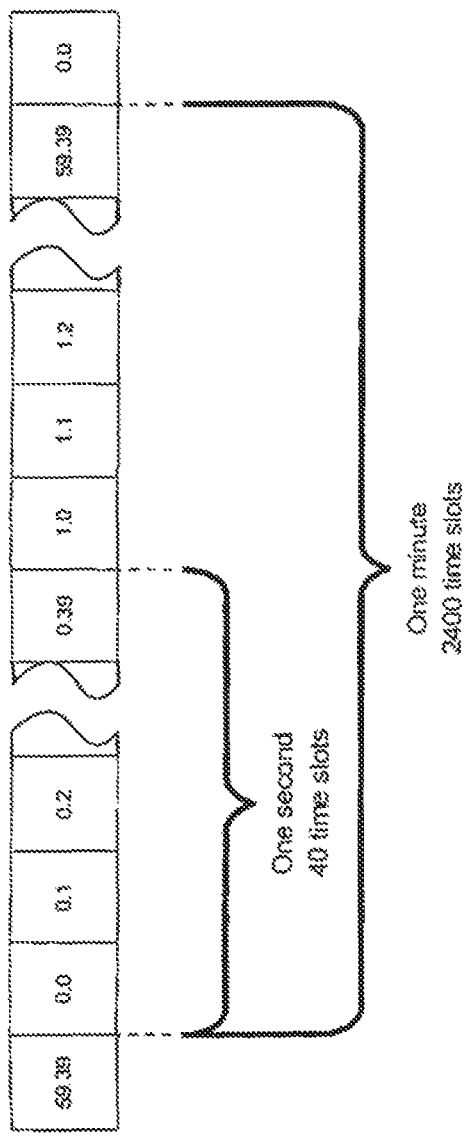
FIG. 13 illustrates the data packet transmit window and time slots for transmission from the transmitter in one embodiment of the present disclosure.

FIG. 13 illustrates the data packet transmit window and time slots for transmission from the transmitter in one embodiment of the present disclosure. In particular, the transmit window in one embodiment of the present disclosure may be configured such that 30 collocated transmitters may operate without any one of them losing data due to transmitter collisions. As discussed in further detail below, to prevent two or more transmitters from continuously colliding, a time hopping mechanism may be implemented to randomize the transmit time.

For example, each minute may be divided into 25 millisecond windows as shown in FIG. 13. As shown in the Figure, a one second window may be divided into 40 time slots, and further, a one minute window may be segmented into 2,400 time slots for transmission. With the transmitter configured to transmit on average once per minute, the data burst is 200 bits long including preamble and a 1 millisecond transmitter warm up, resulting in approximately 25 millisecond burst duration.

Accordingly, in order to prevent transmission from two transmitters from continuously colliding with each other, the transmit time may be offset on each transmission. In one embodiment, the transmit time offset configuration may be implemented as a function of the transmission identification information (TxID) and the transmit time (TxTime).

For example, in one embodiment, with the transmission at once per minute plus 10 seconds, during this 10 second period, 80 time segment windows may be reserved from sensor measurements. Thus since there are 40 transmission windows per each second, the 10 second duration results in 400 transmission windows from which the 80 time segment windows is deducted (for sensor measurement). This results in 320 possible transmission windows to select when to transmit the data packet by the transmitter unit 102. In one embodiment, the transmit time (TxTime) may be 8 bits, and each transmitter may be configured to select a time slot from the 320 possible transmission windows for data transmission. It should also be noted here that once the receiver unit 104 corresponding to a particular transmitter unit 102 is aware of the transmit time (TxTime) associated with the transmitter unit 102, the receiver unit 104 may determine the future transmit window times associated with the transmitter unit 102 without additional information from the transmitter unit 102. This provides substantial advantages, for example, from power savings perspective, in that the receiver unit 104 may substantially accurately anticipate the transmit window for data transmission from the transmitter unit 102, and thus capture and receive substantially all of the transmitted data packets from the transmitter unit 102 without continuously listening out for the transmission data.

Figure 14:
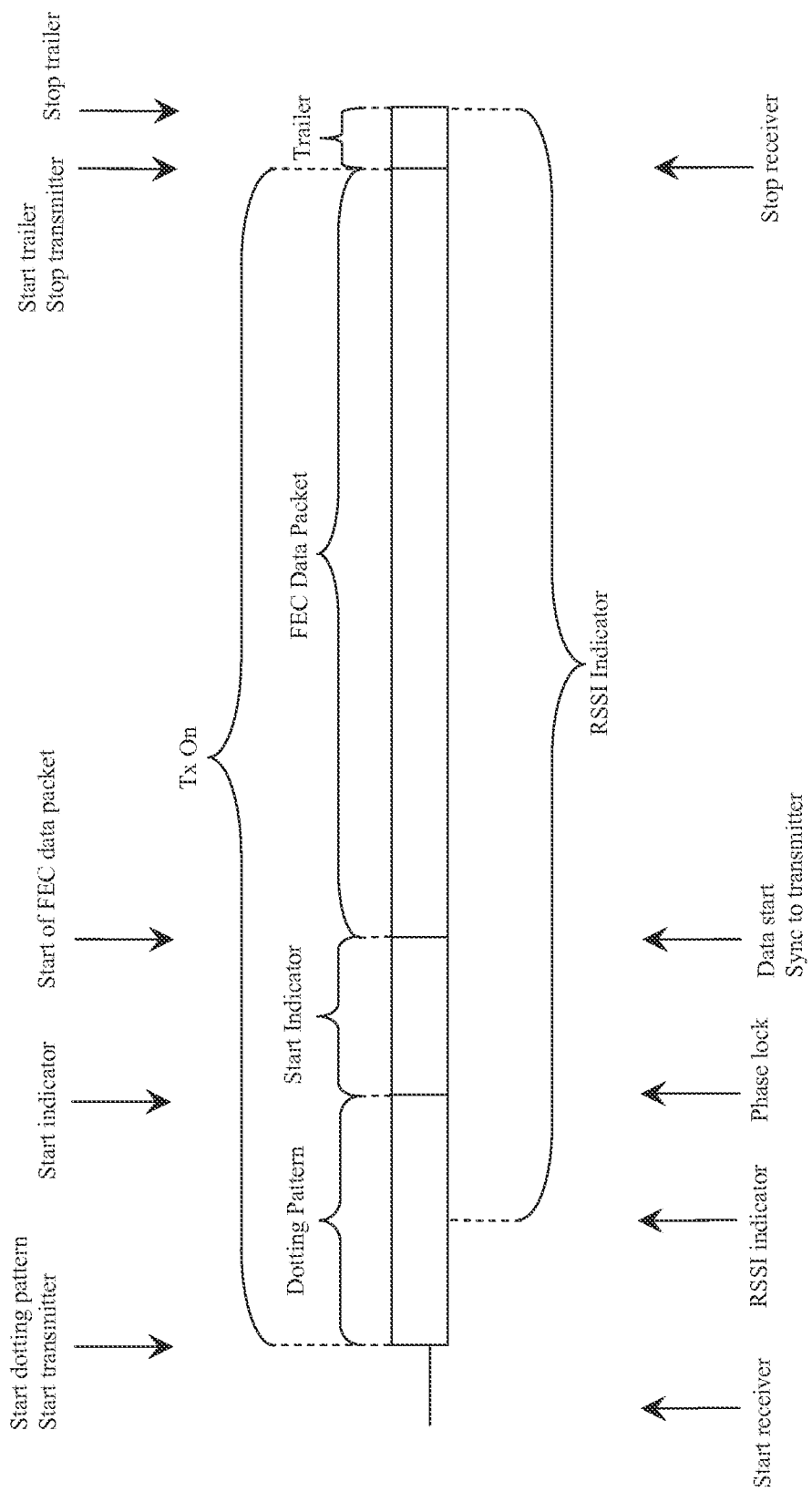
FIG. 14 illustrates the timing of the transmitted data packet transmission by the transmitter and reception by the receiver in one embodiment of the present disclosure.

FIG. 14 illustrates the timing of the transmitted data packet transmission by the transmitter and reception by the receiver in one embodiment of the present disclosure. Referring to the Figure, in one embodiment, the receive window for the receiver unit 104 (FIG. 1) may be configured to be synchronized with the corresponding transmitter when a start indicator of the transmission is detected by the receiver unit 104. For example, the receiver unit 104 may be configured to synchronize the receive window with the associated transmitter unit 102 accurately with a phase locked start indicator. From the phase locked start indicator, the receiver unit 104 may predict the subsequent transmit burst time, with the error being limited to the relative drift between transmissions. When a transmit data packet is missed, the receiver unit 104 may be configured to widen the receive window. In one embodiment, the receive window may be configured relatively narrow so as to maintain the duty cycle low. In the case where the transmitter time drifts substantially to cause the receiver to miss a transmission, the next receive window may be configured to open substantially relatively wide to ensure that the data packet is not missed.

Referring back to the Figures, and each transmission time, the transmitter unit 102 (FIG. 1) is configured to send a data packet which is Manchester encoded, at two Manchester bits per data bit, with 1,900 Manchester bits per second. More specifically, the transmit data packet received by the receiver unit 104 in one embodiment comprises a dotting pattern, a data start indicator, and a forward error correction data as shown in FIG. 14. In one embodiment, the receiver unit 104 may be configured to use the dotting pattern to phase lock to the received signal and to extract the transmitted data clock information.

For optimal accuracy, in one embodiment, the received data should be sampled in the middle of the bit time. The receiver unit 104 needs to maintain phase lock to the data to limit the accumulation of timing error. Referring again to FIG. 14, the start indicator is configured to provide immunity to bit errors during data synchronization. More specifically, after determining the bit time and phase, the receiver unit 104 is configured to start collecting and saving the received data bits. The receiver unit 104 may be configured to search the received bit stream for data start indicator. In one embodiment, a 12-bit start indicator may be immune to all 2 bit errors. In other words, the receiver unit 104 may be configured such that it does not false detect or miss the start indicator with up to 2 bit errors. In one embodiment, a 13 bit start indicator may be used.

Referring again to FIG. 14, the transmitter identification information (TxID) may in one embodiment be used to schedule transmit time. As discussed above, the transmitter identification information (TxID) may be included in the forward error correction parity determination, and not transmitted with the transmission data packet.

Furthermore, the receiver unit 104 may be configured to discard a data packet when one of the following error conditions is detected. First, the receiver unit 104 may be configured to discard the data packet where the Reed-Solomon decoding procedure indicates that the data packet is uncorrectable. Second, after decoding, the receiver unit 104 may be configured to verify that all of the zero pad symbols are zero. A non-zero indicates that the Reed-Solomon decode procedure has inadvertently "corrected" a pad byte from zero to some other value. In this case, the receiver unit 104 is configured to discard the associated data packet.

Third, after decoding, the receiver unit 104 is configured to verify that the transmitter identification information (TxID) pad symbols correspond to the correct transmitter identification information (TxID). Again, an incorrect value representing the transmitter identification information (TxID) indicates that the Reed-Solomon decode procedure has inadvertently "corrected" a pad byte to some other value. In this case, as before, the receiver unit 104 is configured to discard the data packet associated with the incorrect transmitter identification information (TxID). Finally, an unexpected value associated with the transmit time (TxTime) for the data packet will indicate an error, since the transmit time (TxTime) is a predictable and determinable value, and which increments for every packet transmitted, as discussed above. In this case, the receiver unit 104 is configured to discard the data packet associated with the unexpected transmit time (TxTime) value.

Furthermore, in certain cases, the receiver unit 104 may be prevented from receiving the correct data from an in range transmitter 102. These include missed data synchronization, uncorrectable data packet due to random noise, and uncorrectable data packet due to burst noise. On average, at worst received signal strength, the receiver unit 104 may miss one data packet every 1.7 days. Burst noise is a function of the physical location, including the colliding of two transmitters that have overlapping transmission range. As discussed herein, the time hopping procedure makes it less likely that two transmitters will collide several times consecutively.

FIG. 15 illustrates a data packet at the receiver for demodulation in accordance with one embodiment of the present disclosure. As discussed above, the receiver unit 104 (FIG. 1) in one embodiment may be configured to demodulate or extract the data clock from the received signal and to capture the received bit stream. More specifically, during the receiver unit 104 bit synchronization, the receiver unit 104 may be configured to establish phase lock during the leading zeros of the link prefix, to maintain the phase lock during the entire received bit stream, to save the data packet contents with the most significant bit first, or to save the data packet contents byte zero first.

With respect to receiver 104 frame synchronization, the receiver unit 104 in one embodiment may be configured to identify a bit sequence that is a Hamming distance of 2 or less from the transmitted data start indicator (FIG. 14). Moreover, the receiver unit 104 may be configured so that the received bit stream is byte aligned using the first data bit as the first byte boundary.

In one embodiment, the receiver unit 104 may be configured to wait up to 70 seconds for a data packet. The receiver unit 104 may be configured to perform synchronized time hopping with a corresponding transmitter unit 102, and to maintain time hop synchronization for more than 30 minutes, for example, of un-received data packets. Alternatively, the receiver in one embodiment may be configured to maintain time hop synchronization with the relative temperature changes of the transmitter and receiver from the minimum and maximum crystal frequency extremes, which tests the ability of the receiver unit 104 to track the transmitter unit 102 time base as the crystal frequency of both devices changes with temperature.

Referring back to the Figures, the receiver unit 104 is configured to perform Reed-Solomon decode procedure to the received data packet received from the transmitter unit 102. More specifically, the receiver unit 104 in one embodiment is configured to build the Reed-Solomon data block contents as shown in FIG. 11 from the data packet received from the transmitter unit 102. Again, the packed data are the first 15 bytes of the received packet, and the parity symbols are the next 6 bytes. The zero pad bytes are set to zero.

Additionally, the receiver unit 104 may be configured to perform error detection and corrections including determining whether the Reed-Solomon decode function returns a success, whether all of the 230 zero pad bytes are still zero, where in each of the cases, the receiver unit 104 is configured to discard the data packet if any of these checks fail. Moreover, in the case where the receiver unit 104 has acquired a corresponding transmitter unit 102, the receiver unit 104 may be configured to check that the 32 bit transmitter identification information (TxID) is correct, and also, whether the transmit window time (TxTime) value is accurate (i.e., incrementing every minute). If any of these checks fail, the receiver unit 104 flags an error, and is configured to discard the data packet associated with the error.

Figure 16:
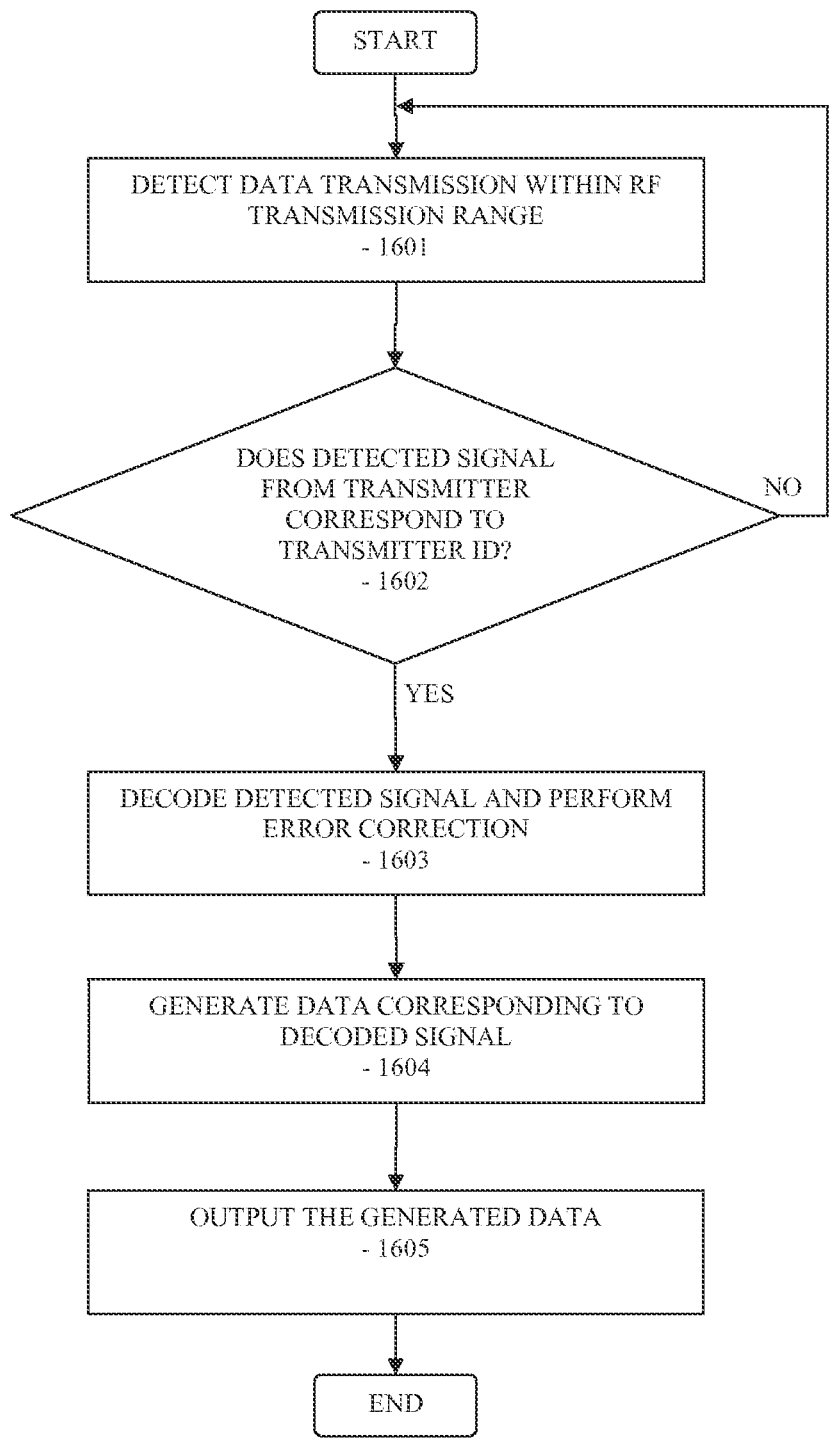
FIG. 16 is a flowchart illustrating the transmitter/receiver communication of the system shown in FIG. 1 in accordance with one embodiment.

FIG. 16 is a flowchart illustrating the transmitter/receiver communication of the system shown in FIG. 1 in accordance with one embodiment. Referring to FIG. 16, upon completing the power up procedure as discussed above, the receiver unit 104 (FIG. 1) listens for the presence of a transmitter within the RF communication link range. When the transmitter unit 102 is detected within the RF communication link range at step 1601, in one embodiment, the receiver unit 104 may be configured to receive and store the identification information corresponding to the detected transmitter unit 102. Alternatively, the receiver unit 104 may be pre-configured with the corresponding transmitter identification information, and thus, will be configured to verify the transmitter identification based on the data transmission received detected at step 1601. More specifically, at step 1601, the receiver unit 104 may be configured to detect (or sample) data transmission within its RF communication range. In one aspect, the receiver unit 104 may be configured to identify a positive data transmission upon ascertaining that the data transmission is above a predetermined strength level for a given period of time (for example, receiving three separate data signals above the predetermined strength level from the transmitter unit 102 at one minute intervals over a period of five minutes).

At step 1602, the receiver 104 is configured to determine whether the detected signals within the RF communication range is transmitted from the transmitter unit 102 having the transmitter identification information stored or reconstructed (e.g., regenerated) in the receiver unit 104. If it is determined at step 1602 that the detected data transmission at step 1601 does not originate from the transmitter corresponding to the transmitter identification information, then the procedure returns to step 1601 and waits for the detection of the next data transmission.

On the other hand, if at step 1602 it is determined that the detected data transmission is from the transmitter unit 102 corresponding to the transmitter identification information, then at step 1603, the receiver proceeds with decoding the received data and performing error correction thereon. In one embodiment, the receiver is configured to perform Reed-Solomon decoding, where the transmitted data received by the receiver is encoded with Reed-Solomon encoding. Furthermore, the receiver is configured to perform forward error correction to minimize data error due to, for example, external noise, and transmission noise.

Referring back to FIG. 16, after decoding and error correcting the received data, the receiver unit 104 (FIG. 1) at step 1604 generates output data corresponding to the decoded error corrected data received from the transmitter unit 102, and thereafter, at step 1605, the receiver unit 104 outputs the generated output data for the user as a real time display of the output data, or alternatively, in response to the user operation requesting the display of the output data. Additionally, before displaying the output data for the user, other pre-processing procedures may be performed on the output data to, for example, smooth out the output signals. In one aspect, the generated output data may include a visual graphical output displayed on the graphical user interface of the receiver. Alternatively, the output data may be numerically displayed representing the corresponding glucose level.

Referring to FIGS. 1 and 16, in one aspect of the present disclosure, the generated data output at step 1605 may be provided to the medication delivery unit 106 (FIG. 1) for analysis and therapy management, such as bolus calculations and basal profile modifications to alter or otherwise adjust the level of insulin dosage administered to the patient via the medication delivery unit 106 which may include an insulin pump.

Referring again to the Figures discussed above, the time hopping procedure of one embodiment is described. More specifically, since more than one transmitter unit 102 (FIG. 1) may be within the receiving range of a particular receiver unit 104, and each transmitting data every minute on the same frequency, transmitter units 102 are configured to transmit data packets at different times to avoid co-location collisions (that is, where one or more receiver unit 104 cannot discern the data signals transmitted by their respective associated transmitter units 102 because they are transmitting at the same time).

In one aspect, transmitter unit 102 is configured to transmit once every minute randomly in a window of time of plus or minus 5 seconds (i.e., it time hops.) To conserve power, receiver unit 104 does not listen for its associated transmitter unit 102 during the entire 10 second receive window, but only at the predetermined time the receiver unit 104 knows the data packet will be coming from the corresponding transmitter unit 102. In one embodiment, the 10 second window is divided into 400 different time segments of 25 milliseconds each. With 80 time segments reserved for sensor measurements as discussed above, there remain 320 time segments for the transmission. Before each RF transmission from the transmitter unit 102 takes place, both the transmitter unit 102 and the receiver unit 104 are configured to recognize in which one of the 320 time segments the data transmission will occur (or in which to start, if the transmission time exceeds 25 milliseconds). Accordingly, receiver unit 104 only listens for a RF transmission in a single 25 millisecond time segment each minute, which varies from minute to minute within the 10 second time window.

Moreover, each transmitter unit 102 is configured to maintain a "master time" clock that the associated receiver unit 104 may reference to each minute (based on the time of transmission and known offset for that minute). A counter on the transmitter unit 102 may be configured to keep track of a value for transmit time (TxTime) that increments by 1 each minute, from 0 to 255 and then repeats. This transmit time (TxTime) value is transmitted in the data packet each minute, shown as byte 0 in FIG. 9. Using the transmit time (TxTime) value and the transmitter's unique identification information, both the transmitter unit 102 and the receiver unit 104 may be configured to calculate which of the 320 time segments will be used for the subsequent transmission. In one embodiment, the function that is used to calculate the offset from the master clock 1-minute tick is a pseudo-random number generator that uses both the transmit window (TxTime) and the transmitter identification information (TxID) as seed numbers. Accordingly, the transmission time varies pseudo-randomly within the 10 second window for 256 minutes, and then repeats the same time hopping sequence again for that particular transmitter unit 102.

In the manner described above, in accordance with one embodiment of the present disclosure, co-location collisions may be avoided with the above-described time hopping procedure. That is, in the event that two transmitters interfere with one another during a particular transmission, they are not likely to fall within the same time segment in the following minute. As previously described, three glucose data points are transmitted each minute (one current and two redundant/historical), so collisions or other interference must occur for 3 consecutive data transmissions for data to be lost. In one aspect, when a transmission is missed, the receiver unit 104 may be configured to successively widen its listening window until normal transmissions from the respective transmitter unit 102 resume. Under this approach, the transmitter listens for up to 70 seconds when first synchronizing with a transmitter unit 102 so it is assured of receiving a transmission from transmitter unit 102 under normal conditions.

Figure 17:
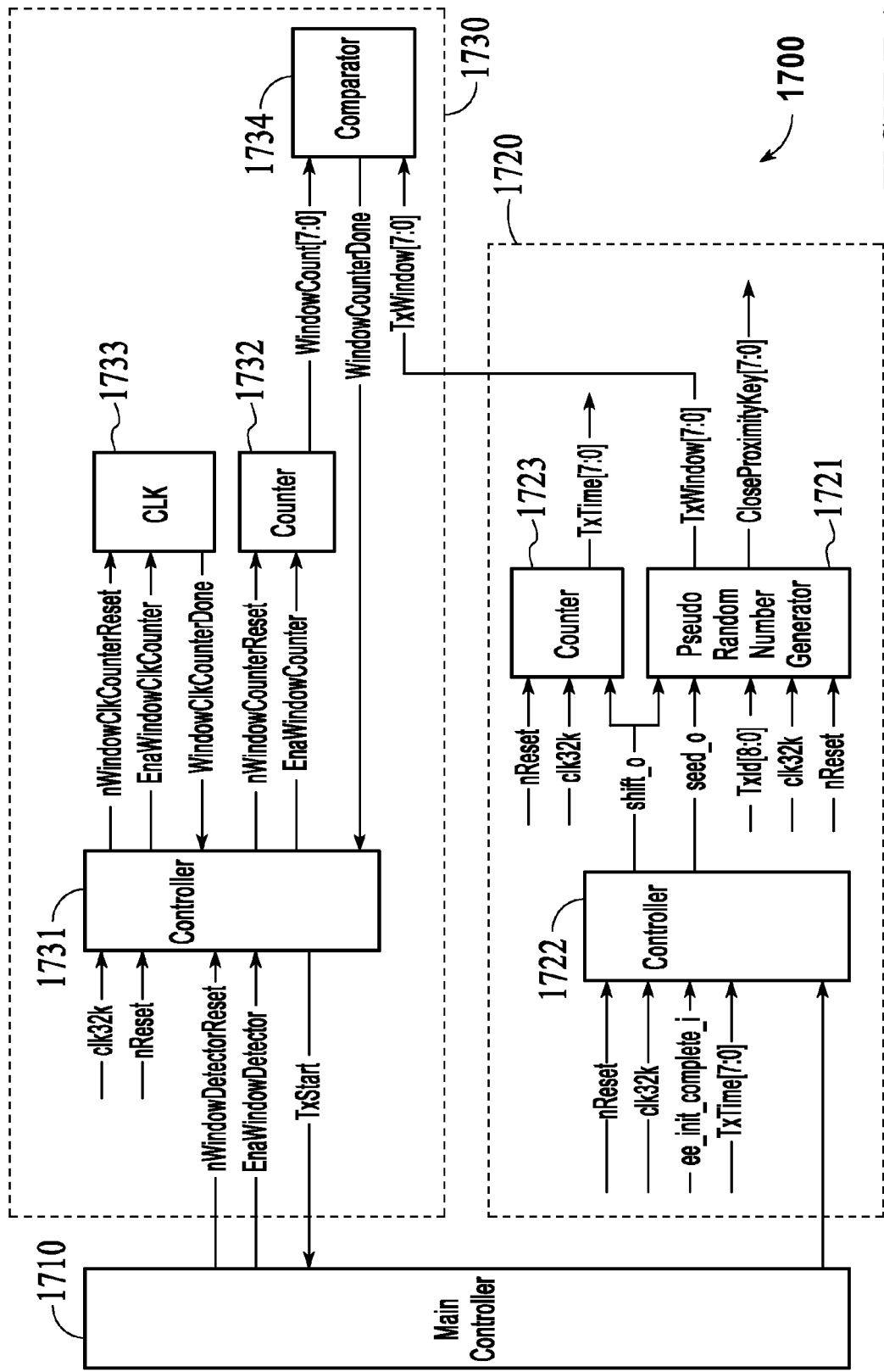
FIG. 17 is a block diagram of a transmit window detector in one embodiment of the present disclosure.

FIG. 17 is a block diagram of a transmit window detector of transmitter unit 102 (FIG. 1) in the analyte monitoring system 100 in one embodiment of the present disclosure. The transmit window detector 1700 in one embodiment may be configured to determine a suitable time window for data transmission in order to avoid transmission interference with other signal transmission devices within range. The transmit window detector 1700, in one embodiment, may be implemented with one or more application specific integrated circuits (ASICs) or is a component of an ASIC used in conjunction with one or more state machines. In another embodiment, the transmit window detector may be a field programmable gate array (FPGA). In one embodiment, the transmit window detector 1700 includes two main components; a window determination module 1720 and a window detection module 1730.

In one embodiment, a transmission interval is partitioned into a plurality of available transmission windows. Each transmission window is of an adequate length of time to allow for application data transmission. In one embodiment, a transmission interval is approximately 6.234 seconds and is partitioned into 255 transmission windows, each approximately 24.45 milliseconds in length. In another embodiment, a transmission interval is approximately 1 minute and is partitioned into approximately 2400 windows, each approximately 25 milliseconds in length.

Referring still to FIG. 17, the transmit window detector 1700 of transmitter unit 102 (FIG. 1) is configured to determine a suitable time window for data transmission. The suitable time window for data transmission, herein $TX_{Window}$, is determined by assigning a particular transmission window of the transmission interval to each transmitter. In one embodiment, the assigned transmission window for a transmitter may vary in each transmission interval. In such a case, the variance of the assigned transmission window may be determined by a pseudo-random assignment of transmission windows. The window determination module 1720 is configured for the determination of the assigned pseudo-random transmission windows. The window determination module 1720 in one embodiment includes a pseudo-random number generator 1721, which in one embodiment is a linear feedback shift register (LFSR). The LFSR configured as a pseudo-random number generator is configured to generate a pseudo-random number, which is used as the value of the assigned transmission window for data transmission by transmitter unit 102.

The window determination module 1720 determines an initial transmission window value ($TX_{Window}$) based on a seed value. In one embodiment, the seed value for the window determination module 1720 is a transmitter identification number ($TX_{ID}$) associated with the particular transmitter. The $TX_{ID}$ is loaded into the pseudo-random number generator 1721 as the initial value from which the pseudo-random number generator 1721 uses for determination of each subsequent generated output value. The pseudo-random number generator 1721 generates a next pseudo-random number for the value of $TX_{Window}$ each time a shift command is received. The shift command signal transmission is controlled by a determination controller component 1722 of the window determination module 1720. In one embodiment the determination controller 1722 is a finite state machine. In other embodiments, the determination controller 1722 may be a switch, a latch, a flip-flop, or the like.

In another embodiment, the window determination module 1720 also includes a determination counter 1723. The determination counter 1723 is operatively coupled to the determination controller 1722. The determination counter 1723 keeps track of the number of different transmission windows that have been assigned based upon the output from the pseudo-random number generator 1721. A pseudo-random number generator 1721 includes a finite number of possible output values based upon the configuration of the pseudo-random number generator 1721. For example, an 8-bit pseudo-random number generator can only generate a total of $2^8$ or 256 different numbers, and because a pseudo-random number generator 1721, such as a LFSR determines a next output value based upon the current or previous output value, eventually the sequence of numbers generated by the pseudo-random number generator 1721 begins to repeat. The determination counter 1723 tracks the number of different numbers generated by the pseudo-random number generator 1721, which in turn corresponds to the number of different transmission windows assigned. In one aspect, when the determination counter 1723 reaches a maximum value, for example the maximum number of different values that can be generated by the pseudo-random number generator 1721, the determination controller 1722 may load a new seed value into the pseudo-random number generator 1721 and the determination counter 1723 may be reset.

Still referring to FIG. 17, once the transmission window for a transmitter has been assigned for a particular transmission interval, a window detection module 1730 is used in order to determine when that transmission window of the transmission interval has arrived. In one embodiment, the window detection module 1730 includes a detection controller 1731 operatively coupled to a detection counter 1732 and a detection clock 1733. In one embodiment, the detection controller 1731 is a finite state machine. The detection controller 1731 compares the current value of the detection counter 1732 to the generated value of $TX_{Window}$ for each transmission window of a transmission interval by use of a comparator 1734 coupled to the detection controller 1731.

When the detection counter 1732 is equal to $TX_{Window}$, the detection controller 1731 determines that the current transmission window of the transmission interval is the assigned transmission window for the transmitter. As such, the detection controller 1731 sends a signal to a main controller 1710 of the transmit window detector 1700, indicating for the transmitter to begin data transmission. If the detection counter 1732 is not equal to $TX_{Window}$, the detection controller 1731 determines it is not currently the assigned transmission window, and no signal to transmit data is sent to the main controller 1710.

The detection counter 1732 is initialized to '1', and is configured to increment by one for each transmission window. The detection counter 1732 determines the passing of a transmission window by receiving a signal from the detection clock 1733, which is configured to count system clock cycles. The detection clock 1733 is configured to count the number of system clock cycles that corresponds to one transmission window. In one embodiment, the detection clock 1733 is configured to count 793 system clock cycles, which may correspond to approximately 24.45 milliseconds. In this case, 24.45 milliseconds is the transmission window.

In one embodiment, when the detection controller 1731 determines the current transmission window is equal to the assigned transmission window, in other words, when the transmitter is configured to transmit, the detection counter 1732 is reset and is configured to not re-activate until a signal is received from the detection controller 1731 indicating the beginning of a new transmission interval. Furthermore, in one aspect, once the detection counter 1732 is reset, the detection clock 1733 enters a stand-by state, and doesn't begin counting system clock cycles again until the detection controller 1731 sends the detection clock 1733 a signal indicating the beginning of a new transmission interval. In another embodiment, the detection clock 1733 continually counts system clock cycles, regardless of whether the detection counter 1732 is activated.

In another embodiment, the detection counter 1732 counts until a maximum value is reached, such as the number of transmission windows of a transmission interval, and upon reaching said maximum value, then the detection counter 1732 is reset. In this configuration, the detection counter 1732 may continuously count, regardless of whether the detection controller 1731 determined that the assigned transmission window had been reached and a data transmission sent.

Figure 18A:
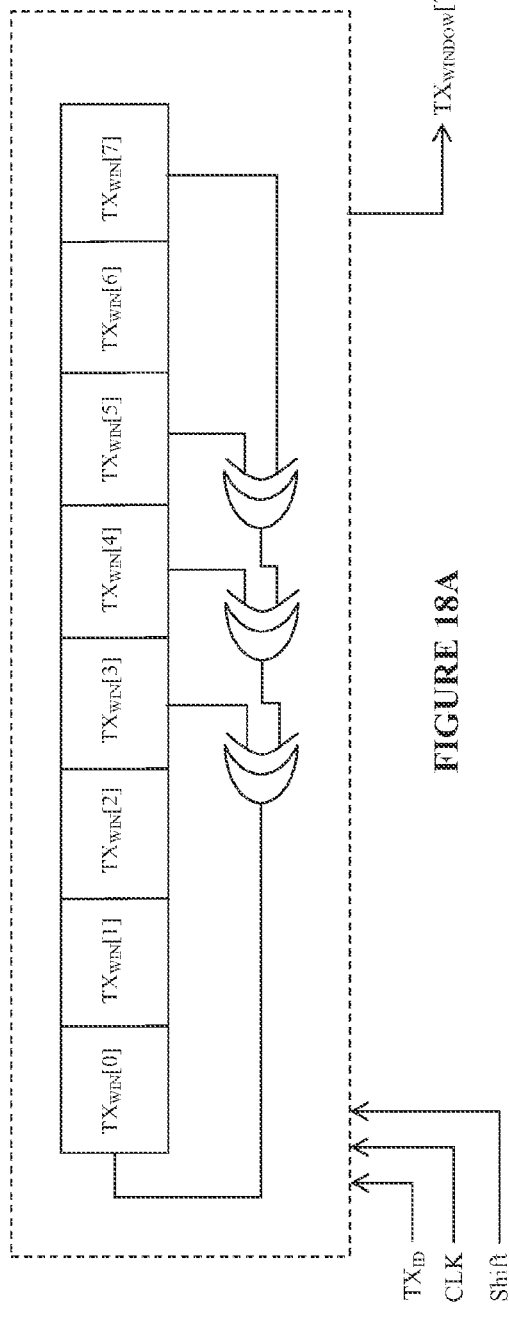
FIGS. 18A and 18B are block diagrams of pseudo-random number generators for use in one or more embodiments of the present disclosure.
Figure 18B:
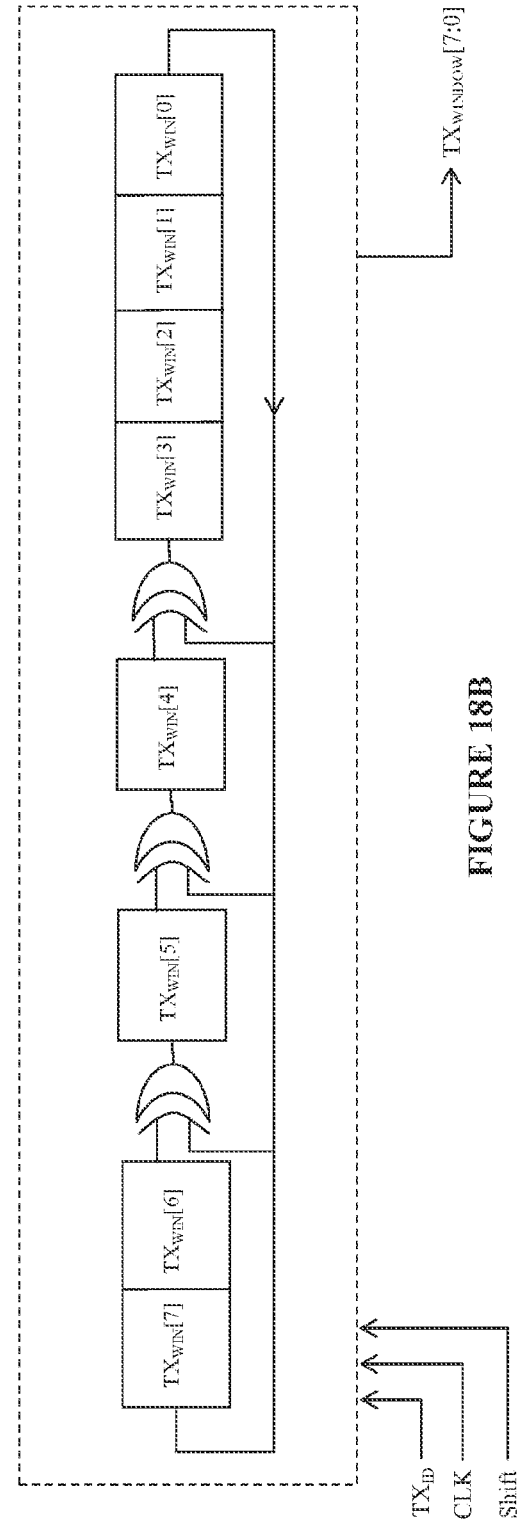

FIGS. 18A and 18B are block diagrams of pseudo-random number generators for use in one or more embodiments of the present disclosure. A pseudo-random number generator may be a linear feedback shift register (LFSR), for example a Fibonacci LFSR as illustrated in FIG. 18A. The LFSR pseudo-random number generator of FIG. 18A is an 8-bit Fibonacci LFSR. In other embodiments, the LFSR may be fewer bits, for example a 4-bit LFSR, or may be more bits, for example a 16-bit LFSR. Each number of bits of the LFSR configured as a pseudo-random number generator corresponds to the number of possible numbers to be generated. For each n bits of the LFSR, a total number of possible output values is $2^n$.

For example, an 8-bit LFSR would result in $2^8$ possible output values, or 256 possible output values. In one aspect, an LFSR is configured such that neither the seed value nor the pseudo-random number generated can be the value of '00000000', thus leaving $2^{n-1}$ (255 for an 8-bit LFSR) possible output values. In one aspect, the '00000000' output value may result in a continual output of the '00000000' state, and thus a failure of the number generation. In one embodiment, the number of possible output values corresponds to the number of transmission windows of a transmission interval.

A linear feedback shift register is configured such that the input value of the LFSR is a linear function of the LFSR's previous output value or state. As such, an LFSR requires a seed value, or initial state value, for implementation. In one embodiment, the LFSR linear function is driven based on OR, exclusive-or (XOR), or inverse-exclusive-or (INV-XOR) functions of one or more bits of the previous output value. The seed value, in one embodiment, may be the transmitter identification, $TX_{ID}$, of the transmitter. The seed value is loaded into the LFSR, as shown in FIGS. 18A and 18B. The output value of the LSFR after input of the seed value is the value of the first $TX_{Window}$.

In the Fibonacci LFSR of FIG. 18A, a total of four bits of the eight bit output value ($TX_{Window}[7:0]$) of the LFSR are the taps, or the feedback bits of the LFSR. For the LFSR to be of maximum length, i.e. for generation of the maximum number of possible output values, there must be an even number of taps, and each tap must be relatively prime, i.e. the greatest common divisor of the taps is 1.

In the case of FIG. 18A, the taps are $TX_{Window}[3]$, $TX_{Window}[4]$, $TX_{Window}[5]$, and $TX_{Window}[7]$. In the configuration of FIG. 18A the feedback polynomial is represented by $p(x)=1+x^4+x^5+x^6+x^8$, where each of the powers of the terms represent the tapped bits, counting from left to right from '1' to 'n' where 'n' is the number of bits. At each command cycle, a linear function is applied to the tapped bits, for example the XOR function, and the resulting output value (either a '1' or a '0') is entered into the first bit, $TX_{Window}[0]$. The subsequent bit values are then shifted right.

For example, if the seed value was 00010000, and a linear XOR function is applied to the seed value using tapped bits $TX_{Window}[3]$, $TX_{Window}[4]$, $TX_{Window}[5]$, and $TX_{Window}[7]$, the output from the linear feedback XOR function would be a '1'. This '1' is then shifted into $TX_{Window}[0]$, and each subsequent bit is shifted to the right such that $TX_{Window}[1] \rightarrow TX_{Window}[2]$, $TX_{Window}[2] \rightarrow TX_{Window}[3]$, and so forth down to $TX_{Window}[6] \rightarrow TX_{Window}[7]$. The result is then a new $TX_{Window}$ value of 10001000. At the next command cycle, the process is repeated. Again, the linear feedback XOR function result is a '1', and again the bit values are shifted resulting in a new $TX_{Window}$ value of 11000100. After another command cycle, the linear feedback XOR function result is again a '1', and the new $TX_{Window}$ value is 11100010, and after another command cycle, the linear feedback XOR function results in a '0', and the new $TX_{Window}$ value is 01110001. This process may continue indefinitely, or alternatively, a new seed value may be implemented at a predetermined time.

Referring to FIG. 18B, in one embodiment, the linear feedback shift register may be a Galois LFSR. The LFSR of FIG. 18B, in one embodiment, is an 8-bit LFSR. The output value of the LFSR is based upon a linear function of the LFSR's previous state, and as such, the LFSR may require the input of an initial seed value. The initial seed value, in one aspect, may be based upon a transmitter identification ($TX_{ID}$). The output value of the LSFR after input of the seed value is the value of the first $TX_{Window}$.

In the Galois LFSR of FIG. 18B, a total of four bits of the eight bit output value ($TX_{Window}[7:0]$) of the LFSR are the taps, or the feedback bits of the LFSR. In the case of FIG. 18B, the taps are $TX_{Window}[3]$, $TX_{Window}[4]$, $TX_{Window}[5]$, and $TX_{Window}[7]$. In the configuration of FIG. 18B the feedback polynomial is represented by $p(x)=1+x^4+x^5+x^6+x^8$ where each of the powers of the terms represent the tapped bits, counting from right to left from '1' to 'n' where 'n' is the number of bits. At each command cycle, the value of the first bit, $TX_{Window}[0]$ is entered into the $n^{th}$ bit, in this case $TX_{Window}[7]$. Each subsequent bit is shifted to the right such that $TX_{Window}[7] \rightarrow TX_{Window}[6]$, $TX_{Window}[6] \rightarrow TX_{Window}[5]$, and so forth down to $TX_{Window}[1] \rightarrow TX_{Window}[0]$.

Furthermore, each tapped bit has a linear function, such as XOR, applied to it in conjunction with the value of the first bit $TX_{Window}[0]$. For example, if the seed value is 00010000, and a linear XOR function is applied in the shift register, the value of $TX_{Window}[0]$, in this case '0', is applied to the $n^{th}$ bit and to the functions of the tapped bits. As such, the new $n^{th}$ bit, $TX_{Window}[7]$ is '0', the new $TX_{Window}[6]$ is '0', the new $TX_{Window}[5]$, based on the output from the XOR of $TX_{Window}[6]$ and $TX_{Window}[0]$, is '0', the new $TX_{Window}[4]$, based on the output from the XOR of $TX_{Window}[5]$ and $TX_{Window}[0]$, is '0', the new $TX_{Window}[3]$, based on the output from the XOR of $TX_{Window}[4]$ and $TX_{Window}[0]$, is '1', the new $TX_{Window}[2]$ '0', the new $TX_{Window}[1]$ is '0', and the new $TX_{Window}[0]$ is '0'. The full result is a $TX_{Window}$ value of 00001000. The same process is repeated at a next command cycle with the new $TX_{Window}$ value as the initial value of the shift register. After the application of the functions, the new value of $TX_{Window}$ is 00000100. The process may continue indefinitely, or alternatively, a new seed value may be implemented at a predetermined time.

In one embodiment, in a Galois LFSR, since the linear functions applied to the tapped bits are independent of one another, the shift functions of a Galois LFSR may be implemented in parallel, thus reducing computation lag time.

In one embodiment, the command cycle for the linear feedback shift register is the transmission interval. The determination controller 1722 (FIG. 17), issues a command signal before the first transmission window of each transmission interval for the pseudo-random number generator 1721 to perform the shift of the LFSR to generate a new pseudo-random number, and thus a new $TX_{Window}$ value.

Referring back to FIG. 17, in one embodiment, each time the determination controller 1722 issues a command signal indicating a new transmission interval and a new pseudo-random number generation, the determination counter 1723 may also be incremented. The determination counter 1723, $TX_{Counter}$, increments by 1 from '1' to a maximum value, such as '255'. The maximum value '255' may be an optimal maximum value for the determination counter 1723 in the case where the pseudo-random number generator 1721 is an 8-bit generator. When $TX_{Counter}$ reaches '255', in one aspect, the pseudo-random number generator 1721 is reloaded with a new seed value.

In one embodiment, the pseudo-random number generator 1721 is coupled to a seed value generator (not shown), which may also be a LFSR configured as a pseudo-random number generator. The seed value generator may generate a new seed value for loading into the pseudo-random number generator 1721 of the window determination module 1720 of the transmit window detector 1700 each time $TX_{Counter}$ reaches '255', or another predetermined maximum value. In yet another embodiment, the determination counter 1723 may be coupled to a number generator, wherein the number generator generates a target number for the determination counter 1723, such that the pseudo-random number generator 1721 of the window determination module 1720 of the transmit window detector 1700 is reset with a new seed value at random, pseudo-random, or predetermined points in time.

In other embodiments, the pseudo-random number generator 1721 of the window determination module 1720 of the transmit window detector 1700 may be more than an 8-bit linear function shift register. In one embodiment, the pseudo-random number generator 1721 may be an 11-bit LFSR. An 11-bit LFSR has a maximum of 2047 different output values, not including the '00000000000' output value. In one aspect, an 11-bit LFSR with 2047 output values, which may correspond to 2047 different transmission windows, may be implemented in a transmitter configuration such that the transmission interval is approximately 1 minute and each transmission window is approximately 25 milliseconds.

In still other embodiments, the pseudo-random number generator 1721 of the window determination module 1720 of the transmit window detector 1700 may be more than an 8-bit LFSR, however, the transmission window $TX_{Window}$ may be only 8-bits of the output from the LFSR. For example, the LFSR may be 9-bits, whereby the initial transmitter identification ($TX_{ID}$) is OR-ed with [0×8] to create a 9-bit input for a 9-bit LFSR. The output may then represent $TX_{Window}$, however, the $TX_{Window}$ to be associated with a transmission window may only be 8-bits of $TX_{Window}$ ($TX_{Window}[7:0]$). In other embodiments, other size LFSRs may be implemented and the number of bits used to determine the transmission window may vary based on the number of available transmission windows.

Figure 19:
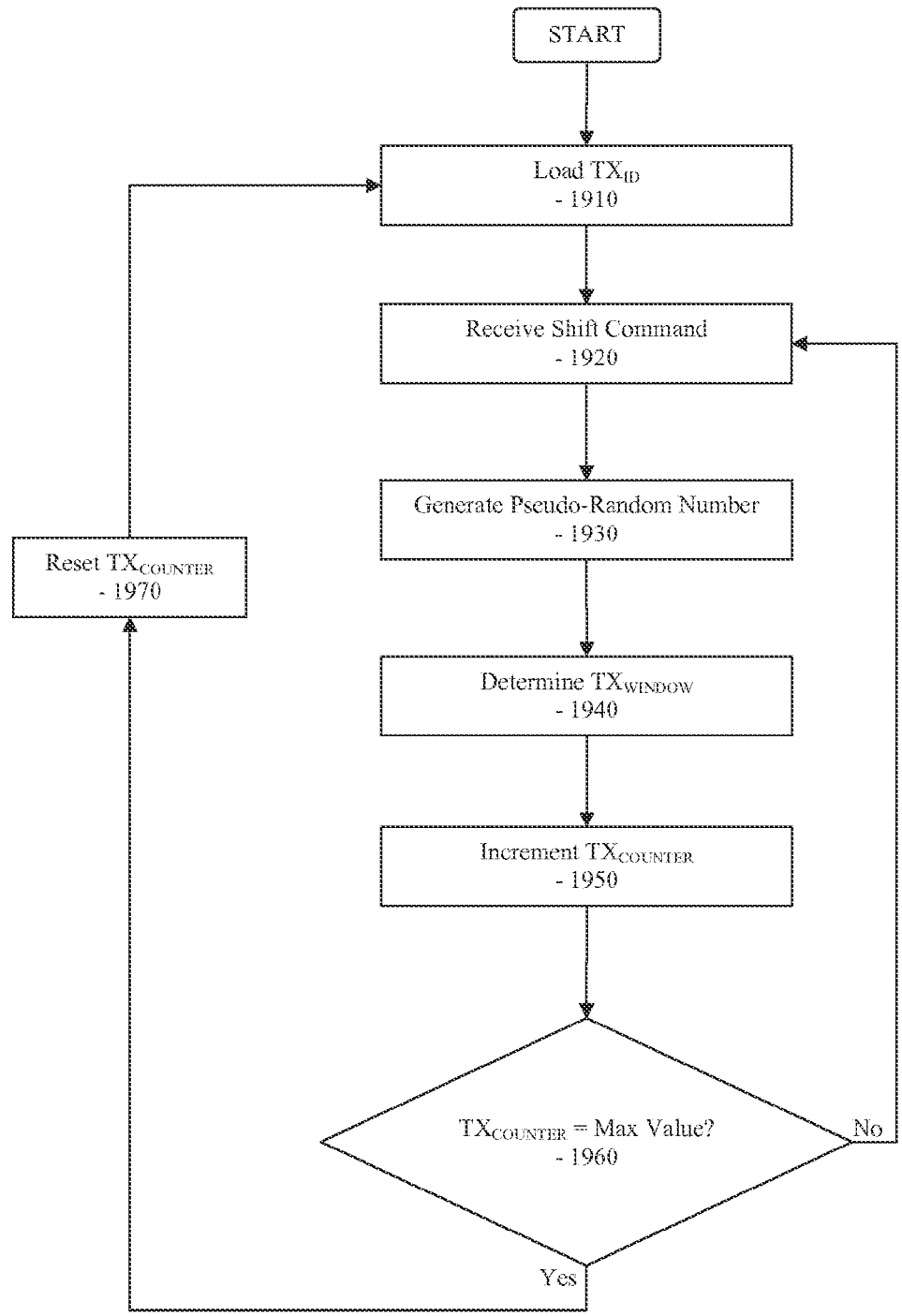
FIG. 19 is a flow chart illustrating transmit window determination in one embodiment of the present disclosure.

FIG. 19 is a flow chart illustrating transmit window determination in one embodiment of the present disclosure. A transmit window determination module 1720 (FIG. 17) may include a pseudo-random number generator 1721, such as a linear feedback shift register as described above in conjunction with FIGS. 18A and 18B. Referring to FIG. 19, in one embodiment, a pseudo-random number generator 1721 of a transmit window determination module 1720, loads an initial seed value, such as a transmitter identification value, $TX_{ID}$ (1910). The initial seed value may, in one aspect, be provided to the pseudo-random number generator 1721 by a determination controller 1722. Once the initial value is loaded into the pseudo-random number generator 1721, a command for a shift in the pseudo-random number generator is received (1920), whereby the shift in the pseudo-random number generator 1721 results in the generation of a next number (1930). The number generated by the pseudo-random number generator 1721 is a transmission window value $TX_{Window}$ (1940).

Furthermore, in one embodiment, a determination counter 1723, $TX_{Counter}$, initialized at 1, increments by one (1950) each time a new $TX_{Window}$ value is generated. $TX_{Counter}$ is configured to continue to increment until a maximum value is reached. In one embodiment, the maximum value of $TX_{Counter}$ is set as the number of different possible output values from the pseudo-random number generator. For example, for an 8-bit pseudo-random number generator, the number of possible different output values is 255, and as such, the maximum value of $TX_{Counter}$ is set at 255. If $TX_{Counter}$ is determined to be at the maximum value (1960), $TX_{Counter}$ is reset back to 1 (1970) and the pseudo-random number generator loads a new initial seed value (1910). In the event that $TX_{Counter}$ is not equal to the maximum value, the pseudo-random number generator 1721 waits to receive a next shift command (1920) and the process is repeated.

In one embodiment, a shift command is sent to and received by the pseudo-random number generator 1721 of the transmit window determination module 1720, every transmission interval. In one aspect, a transmission interval may be approximately 6.234 seconds. In another aspect, a transmission interval may be approximately 1 minute.

Figure 20:
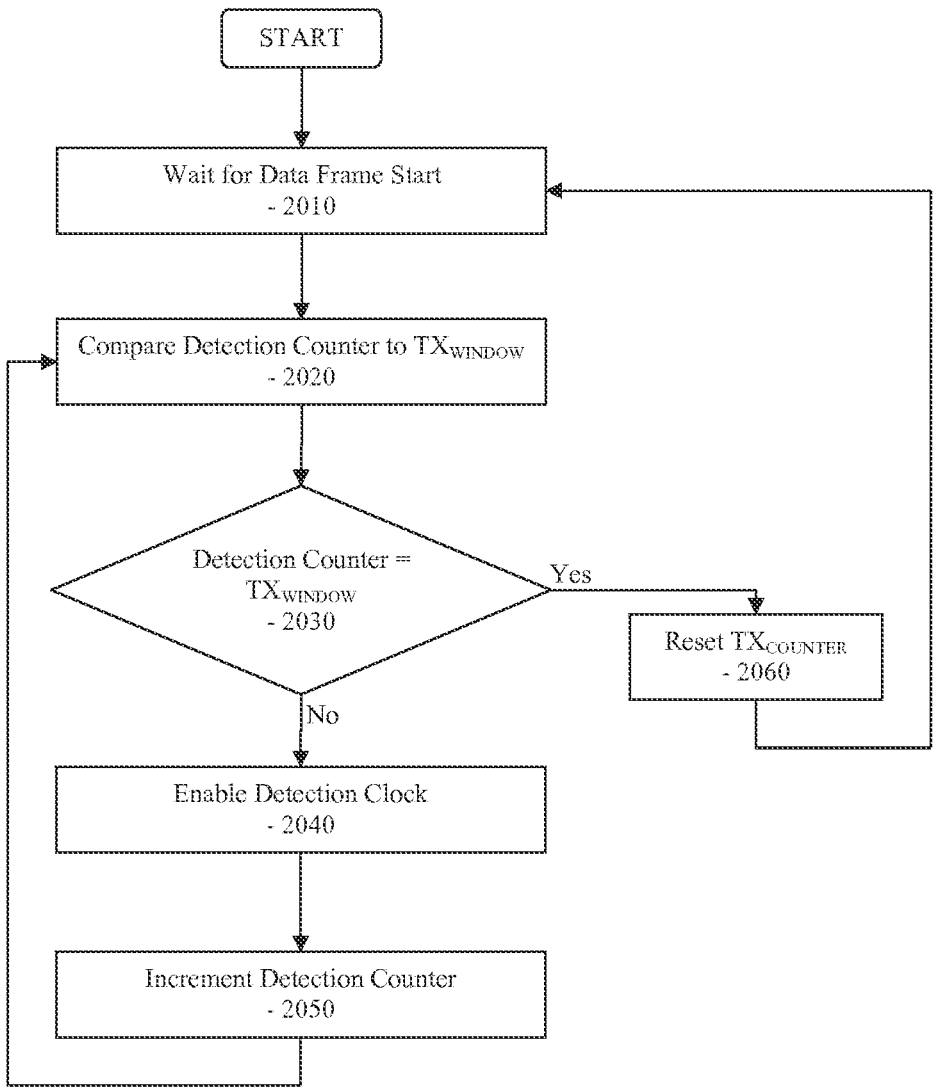
FIG. 20 is a flow chart illustrating transmit window detection in one embodiment of the present disclosure.

FIG. 20 is a flow chart illustrating transmit window detection in one embodiment of the present disclosure. Referring to FIG. 20, a window detection module 1730 (FIG. 17) waits for a data frame start (2010), which may be a start of a transmission interval. After the data frame start, a detector controller 1731 of the window detection module 1730 transitions from an initial state to a state configured to compare the current value of a detection counter 1732 to a current $TX_{Window}$ transmission window value (2020). If the detection counter 1732 value is equal to the $TX_{Window}$ value (2030), the detector controller 1731 transmits a signal to a main controller 1710 to start transmission (2060). If the detection counter 1732 is not equal to $TX_{Window}$, a detection clock 1733 is enabled (2040). The detection clock 1733 counts for the time period of one transmission window plus adequate overhead time. In one embodiment, the transmission window is a time length of 24.45 milliseconds. When the detection clock 1733 reaches a count equivalent to the transmission window time length, which in one embodiment may be a count of 793, the detection counter 1732 is configured to increment by one (2050). The new value of detection counter 1732 is compared again to $TX_{Window}$ (2020) and the process is repeated until the transmission start signal is activated. Once the data transmission is sent, the window detection module 1730 transitions back to a wait mode until the next data frame start.

Referring back to FIG. 17, in one embodiment, the window determination module 1720 may operatively be coupled to a close proximity communication circuit. Output values from the window determination module 1720 are sent to the close proximity communication circuit. Examples of a close proximity detection circuit and communication can be found in U.S. patent application Ser. No. 12/130,995 filed May 30, 2008, now U.S. Pat. No. 7,826,382, entitled "Close Proximity Communication Device and Methods", the disclosure of which is incorporated by reference for all purposes.

In the manner described above, in accordance with the embodiments of the present disclosure, there is provided a continuous glucose monitoring and management system in accordance with one embodiment of the present disclosure including a sensor configured to detect one or more glucose levels, a transmitter operatively coupled to the sensor, the transmitter configured to receive the detected one or more glucose levels, the transmitter further configured to transmit signals corresponding to the detected one or more glucose levels, a receiver operatively coupled to the transmitter configured to receive transmitted signals corresponding to the detected one or more glucose levels, where the transmitter is configured to transmit a current data point and at least one previous data point, the current data point and the at least one previous data point corresponding to the detected one or more glucose levels.

The receiver may be operatively coupled to the transmitter via an RF communication link, and further, configured to decode the encoded signals received from the transmitter.

In one embodiment, the transmitter may be configured to periodically transmit a detected and processed glucose level from the sensor to the receiver via the RF data communication link. In one embodiment, the transmitter may be configured to sample four times every second to obtain 240 data points for each minute, and to transmit at a rate of one data point (e.g., an average value of the 240 sampled data points for the minute) per minute to the receiver.

The transmitter may be alternately configured to transmit three data points per minute to the receiver, the first data point representing the current sampled data, and the remaining two transmitted data points representing the immediately past two data points previously sent to the receiver. In this manner, in the case where the receiver does not successfully receive the sampled data from the transmitter, at the subsequent data transmission, the immediately prior transmitted data is received by the receiver. Thus, even with a faulty connection between the transmitter and the receiver, or a failed RF data link, the present approach ensures that missed data points may be ascertained from the subsequent data point transmissions without retransmission of the missed data points to the receiver.

The transmitter may be configured to encode the detected one or more glucose levels received from the sensor to generate encoded signals, and to transmit the encoded signals to the receiver. In one embodiment, the transmitter may be configured to transmit the encoded signals to the receiver at a transmission rate of one data point per minute. Further, the transmitter may be configured to transmit the current data point and the at least one previous data points in a single transmission per minute to the receiver. In one aspect, the current data point may correspond to a current glucose level, and where at least one previous data point may include at least two previous data points corresponding respectively to at least two consecutive glucose levels, the one of the at least two consecutive glucose levels immediately preceding the current glucose level.

In a further embodiment, the receiver may include an output unit for outputting the received transmitted signals corresponding to one or more glucose levels. The output unit may include a display unit for displaying data corresponding to the one or more glucose levels, where the display unit may include one of a LCD display, a cathode ray tube display, and a plasma display.

The displayed data may include one or more of an alphanumeric representation corresponding to the one or more glucose levels, a graphical representation of the one or more glucose levels, and a three-dimensional representation of the one or more glucose levels. Moreover, the display unit may be configured to display the data corresponding to the one or more glucose levels substantially in real time.

Further, the output unit may include a speaker for outputting an audio signal corresponding to the one or more glucose levels.

In yet a further embodiment, the receiver may be configured to store identification information corresponding to the transmitter.

The receiver may be further configured to perform a time hopping procedure for synchronizing with the transmitter. Alternatively, the receiver may be configured to synchronize with the transmitter based on the signal strength detected from the transmitter, where the detected signal strength exceeds a preset threshold level.

The transmitter in one embodiment may be encased in a substantially water-tight housing to ensure continuous operation even in the situation where the transmitter is in contact with water.

Furthermore, the transmitter may be configured with a disable switch which allows the user to temporarily disable the transmission of data to the receiver when the user is required to disable electronic devices, for example, when aboard an airplane. In another embodiment, the transmitter may be configured to operate in an additional third state (such as under Class B radiated emissions standard) in addition to the operational state and the disable state discussed above, so as to allow limited operation while aboard an airplane yet still complying with the Federal Aviation Administration (FAA) regulations. Additionally, the disable switch may also be configured to switch the transmitter between various operating modes such as fully functional transmission mode, post-manufacture sleep mode, and so on. In this manner, the power supply for the transmitter is optimized for prolonged usage by effectively managing the power usage.

Furthermore, the transmitter may be configured to transmit the data to the receiver in predetermined data packets, encoded, in one embodiment, using Reed-Solomon encoding, and transmitted via the RF communication link. Additionally, in a further aspect of the present disclosure, the RF communication link between the transmitter and the receiver of the continuous glucose monitoring system may be implemented using a low cost, off the shelf remote keyless entry (RKE) chip set.

The receiver in an additional embodiment may be configured to perform, among others, data decoding, error detection and correction (using, for example, forward error correction) on the encoded data packets received from the transmitter to minimize transmission errors such as transmitter stabilization errors and preamble bit errors resulting from noise. The receiver is further configured to perform a synchronized time hopping procedure with the transmitter to identify and synchronize with the corresponding transmitter for data transmission.

Additionally, the receiver may include a graphical user interface (GUI) for displaying the data received from the transmitter for the user. The GUI may include a liquid crystal display (LCD) with backlighting feature to enable visual display in dark surroundings. The receiver may also include an output unit for generating and outputting audible signal alerts for the user, or placing the receiver in a vibration mode for alerting the user by vibrating the receiver.

More specifically, in a further aspect, the receiver may be configured to, among others, display the received glucose levels on a display section of the receiver either in real time or in response to user request, and provide visual (and/or auditory) notification to the user of the detected glucose levels being monitored. To this end, the receiver is configured to identify the corresponding transmitter from which it is to receive data via the RF data link, by initially storing the identification information of the transmitter, and performing a time hopping procedure to isolate the data transmission from the transmitter corresponding to the identification information and thus to synchronize with the transmitter. Alternatively, the receiver may be configured to identify the corresponding transmitter based on the signal strength detected from the transmitter, determined to exceed a preset threshold level.

A method in accordance with one embodiment of the present disclosure includes the steps of receiving an identification information corresponding to a transmitter, detecting data within a predetermined RF transmission range, determining whether the detected data is transmitted from the transmitter, decoding the detected data, and generating an output signal corresponding to the decoded data.

In one embodiment, the step of determining whether the detected data transmission is transmitted from the transmitter may be based on the received identification information. In another embodiment, the step of determining whether the detected data transmission is transmitted from the transmitter may be based on the signal strength and duration of the detected data within the predetermined RF transmission range.

In a further embodiment, the step of decoding may also include the step of performing error correction on the decoded data. Moreover, the step of decoding may include the step of performing Reed-Solomon decoding on the detected data.

Additionally, in yet a further embodiment of the present disclosure, transmitter identification information may not be included in the transmitted data from the transmitter to the receiver. Rather, the receiver may be configured to determine the transmitter identification information from the received data by using Reed-Solomon decoding. More specifically, when decoding the first data packet received from a transmitter, the receiver may be configured to set the value corresponding to the transmitter identification information to zero, and to indicate to the Reed-Solomon decoder that the transmitter identification information is known to be incorrect. The Reed-Solomon decoder may then be configured to use this information to more effectively "correct" during the error correction procedure, and therefore to recover the transmitter identification information from the received data. Indeed, in subsequent data packets, the received pads and the received data packet with the known transmitter identification information are used to facilitate with the error detection.

In the manner described, the present disclosure provides a continuous glucose monitoring system that is simple to use and substantially compact so as to minimize any interference with the user's daily activities. Furthermore, the continuous glucose monitoring system may be configured to be substantially water-resistant so that the user may freely bathe, swim, or enjoy other water related activities while using the monitoring system. Moreover, the components comprising the monitoring system including the transmitter and the receiver are configured to operate in various modes to enable power savings, and thus enhancing post-manufacture shelf life.

In one embodiment, a data monitoring and management system may include a communication link, a transmitter operatively coupled to the communication link, the transmitter configured to transmit a data packet, and a receiver operatively coupled to the communication link, the receiver configured to receive the transmitted data packet, wherein the transmitter is configured to transmit the data packet during an assigned transmission window.

The communication link may include an RF communication link.

In one aspect, a transmit window detector may be operatively coupled to the transmitter, wherein the transmit window detector may be configured to assign the transmission window.

The transmit window detector may include a pseudo-random number generator configured to output a pseudo-random number, which may include a linear feedback shift register, or an 8-bit pseudo-random number generator.

The output of the pseudo-random number generator may correspond to the assigned transmission window.

The transmit window detector may be configured to detect the occurrence of the assigned transmission window.

The transmit window detector may be configured to send a signal to the transmitter upon detection of the occurrence of the assigned transmission window, wherein the signal is an instruction to the transmitter to transmit the data packet.

In another embodiment, a method for transmitting a data packet may include assigning a transmission window of a transmission interval for transmission of a data packet, detecting the occurrence of the transmission window, and transmitting the data packet.

The transmission window may be 24.45 milliseconds.

The transmission interval may be approximately 6.234 seconds and include 255 transmission windows.

In one aspect, assigning a transmission window may comprise generating a pseudo-random number corresponding to the assigned transmission window.

Moreover, a new transmission window may be assigned for each transmission interval.

Furthermore, detecting the occurrence of the transmission window may include maintaining a counter of transmission windows until the counter equals the assigned transmission window.

The counter may be incremented each time a clock reaches a value corresponding to the length of one transmission window.

In one aspect of the present disclosure, an apparatus includes a data stream generator that generates a data stream associated with a monitored analyte level, and a radio frequency logic portion operatively coupled to the data stream generator, the radio frequency logic portion configured to generate a radio frequency data stream based on the data stream generated from the data stream generator, the radio frequency logic portion further including one or more finite state machines and a plurality of discrete digital logic circuits, the one or more finite state machines configured to control the plurality of digital logic circuits to generate the radio frequency data stream for wireless communication.

In certain embodiments, the one or more finite state machines of the radio frequency logic portion includes a serializer state machine configured to transition between a first state and a second state, serially outputting data with the transition.

In certain embodiments, the monitored analyte level is monitored by an analyte sensor.

In certain embodiments, the one or more finite state machines includes a transmit state machine configured to control the generation of the radio frequency data stream.

In certain embodiments, the data stream generator includes a data multiplexer to multiplex data packets associated with the monitored analyte level.

Further, in certain embodiments, the data stream generator further includes a packet engine, wherein the data multiplexer and the packet engine are configured to store the data packets prior to the generation of the radio frequency data stream.

In certain embodiments, the one or more finite state machines of the radio frequency logic portion includes an application specific integrated circuit.

In certain embodiments, the application specific integrated circuit is implemented as a single semiconductor chip.

Certain embodiments also include a radio frequency communication component operatively coupled to the radio frequency logic portion to wirelessly communicate the generated radio frequency data stream to a remote location.

Further, in certain embodiments, the radio frequency communication component includes an antenna configured to transmit radio frequency signals generated based on the radio frequency data stream.

In certain embodiments, the radio frequency logic portion includes one or more of a radio frequency logic finite state machine, a multiplexer, a Reed-Solomon encoder, a clock circuit, a plurality of registers, a counter or a Manchester encoder.

Moreover, in certain embodiments, the radio frequency logic finite state machine is configured for operation in the 26 MHz clock domain.

In certain embodiments, the radio frequency logic portion is configured as a data interface to a radio frequency transmitter, and configured to move data from a data multiplexer operating in a 32 KHz clock domain to a plurality of radio frequency data registers operating in a 26 MHz clock domain.

In another aspect of the present disclosure, a method includes generating a data stream associated with a monitored analyte level with a data stream generator, and operatively coupling a radio frequency logic portion to the data stream generator, the radio frequency logic portion configured to generate a radio frequency data stream based on the data stream generated from the data stream generator, the radio frequency logic portion further including one or more finite state machines and a plurality of discrete digital logic circuits, the one or more finite state machines configured to control the plurality of digital logic circuits to generate the radio frequency data stream for wireless communication.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present disclosure and that structures and methods within the scope of these claims and their equivalents be covered thereby.

What is claimed is:

1. A system comprising:
    an analyte sensor configured to provide a signal representative of a monitored analyte level; and
    sensor electronics couplable to the analyte sensor to implement one or more finite state machines to receive the signal from the analyte sensor and to generate a data stream for transmission, the one or more finite state machines including a serializer state machine to transition between a first state and a second state, and for serially outputting data with the transition.

2. The system of claim 1, wherein the one or more finite state machines includes a transmit state machine to control generating the data stream.

3. The system of claim 1, wherein the sensor electronics includes multiplexing function to multiplex data packets associated with the monitored analyte level.

4. The system of claim 3, wherein the sensor electronics further includes packet engine function, wherein the multiplexing and packet engine functions store the data packets prior to the generation of the data stream.

5. The system of claim 1, wherein the one or more finite state machines of the sensor electronics includes an application specific integrated circuit.

6. The system of claim 5, wherein the application specific integrated circuit is implemented as a single semiconductor chip.

7. The system of claim 1 further including a radio frequency communication component operatively coupled to the sensor electronics to wirelessly communicate the generated data stream to a remote location, wherein the radio frequency communication component includes an antenna configured to transmit radio frequency signals generated based on the data stream, wherein the sensor electronics include one or more of a clock circuit, a plurality of registers, or a counter, and further, wherein the sensor electronics implements a radio frequency logic finite state machine to operate in a predetermined clock domain.

8. The system of claim 1 wherein the sensor electronics is positionable on a user's body with at least a portion of the analyte sensor disposed subcutaneously.

9. The system of claim 1, wherein the analyte sensor includes a plurality of electrodes, wherein the plurality of electrodes include a working electrode comprising an analyte-responsive enzyme bonded to a polymer disposed on the working electrode.

10. The system of claim 9, wherein the analyte-responsive enzyme is chemically bonded to the polymer disposed on the working electrode.

11. A method, comprising:
    generating a signal representative of a monitored analyte level from an analyte sensor;
    operatively coupling sensor electronics to the analyte sensor, the sensor electronics configured to implement one or more finite state machines to receive the signal from the analyte sensor and to generate a data stream for transmission; and
    providing a serializer state machine which transitions between a first state and a second state, and for serially outputting data with the transition.

12. The method of claim 11, further including controlling the generation of the data stream with a transmit state machine.

13. The method of claim 11, further including multiplexing data packets associated with the monitored analyte level with a data multiplexer.

14. The method of claim 13, further including storing the data packets prior to the generation of the data stream with a packet engine and the data multiplexer.

15. The method of claim 11 further including providing an application specific integrated circuit including the one or more finite state machines of the sensor electronics.

16. The method of claim 15, wherein the application specific integrated circuit is implemented as a single semiconductor chip.

17. The method of claim 11, further including operatively coupling a radio frequency communication component to the sensor electronics to wirelessly communicate the generated data stream to a remote location;

providing an antenna configured to transmit radio frequency signals generated based on the data stream; and configuring a radio frequency logic finite state machine for operation at a predetermined clock domain.

18. The method of claim 11, further including positioning the sensor electronics on a body of a user with at least a portion of the analyte sensor disposed subcutaneously.

19. The method of claim 11, wherein the analyte sensor includes a plurality of electrodes, wherein the plurality of electrodes include a working electrode comprising an analyte-responsive enzyme bonded to a polymer disposed on the working electrode.

20. The method of claim 19, wherein the analyte-responsive enzyme is chemically bonded to the polymer disposed on the working electrode.

* * * * *